(12) United States Patent
Imahori et al.

(10) Patent No.: US 12,358,865 B2
(45) Date of Patent: Jul. 15, 2025

(54) COMPOUND, CARBON DIOXIDE ABSORPTION/RELEASE AGENT, CARBON DIOXIDE COLLECTION METHOD, AND CARBON DIOXIDE COLLECTION APPARATUS

(71) Applicant: Tokyo University of Science Foundation, Tokyo (JP)

(72) Inventors: Tatsushi Imahori, Tokyo (JP); Ryo Motoyama, Tokyo (JP)

(73) Assignee: Tokyo University of Science Foundation, Tokyo (JP)

( * ) Notice: Subject to any disclaimer, the term of this patent is extended or adjusted under 35 U.S.C. 154(b) by 881 days.

(21) Appl. No.: 17/434,579

(22) PCT Filed: Feb. 28, 2020

(86) PCT No.: PCT/JP2020/008552
§ 371 (c)(1),
(2) Date: Aug. 27, 2021

(87) PCT Pub. No.: WO2020/175711
PCT Pub. Date: Sep. 3, 2020

(65) Prior Publication Data
US 2022/0144757 A1 May 12, 2022

(30) Foreign Application Priority Data

Feb. 28, 2019 (JP) ................. 2019-036824

(51) Int. Cl.
*C07C 245/08* (2006.01)
*B01D 53/02* (2006.01)
(Continued)

(52) U.S. Cl.
CPC ............ *C07C 245/08* (2013.01); *B01D 53/62* (2013.01); *B01D 2253/20* (2013.01)

(58) Field of Classification Search
None
See application file for complete search history.

(56) References Cited

U.S. PATENT DOCUMENTS

| 2005/0038284 A1 | 2/2005 | Matsumoto et al. |
| 2010/0126348 A1 | 5/2010 | Shimizu et al. |
| 2015/0190784 A1 | 7/2015 | Ladewig et al. |

FOREIGN PATENT DOCUMENTS

| JP | 2003146944 A | 5/2003 |
| JP | 2015529550 A | 10/2015 |
| WO | 2009001804 A1 | 12/2008 |

OTHER PUBLICATIONS

PubChem CID 88839196, National Center for Biotechnology Information. "PubChem Compound Summary for CID 88839196, 4-(4-Phenyldiazenylphenyl)naphthalen-1-amine" PubChem, https://pubchem.ncbi.nlm.nih.gov/compound/4-_4-Phenyldiazenylphenyl_naphthalen-1-amine. Accessed Jul. 17, 2024, create date Feb. 13, 2015. (Year: 2015).*

(Continued)

*Primary Examiner* — Daniel Berns
(74) *Attorney, Agent, or Firm* — Banner & Witcoff, Ltd.

(57) ABSTRACT

A compound represented by Formula (1): each of $L^1$ and $L^2$ independently represents an alkyl group having from 1 to 20 carbon atoms, an alkoxy group having from 1 to 20 carbon atoms, $NH_2$, $NHR^3$, $NR^3R^4$, an ester group, a carboxy group, an amide group, a cyano group, a nitro group, a halogen atom, an acyl group, $CF_3$, $O(CH_2)_fOCH_3$, a carbamate group, or an aryl group. l represents 1 or 2. Each of $R^1$ and $R^2$ independently represents a divalent hydrocarbon group having from 1 to 10 carbon atoms, at least one hydrogen atom of the divalent hydrocarbon group is optionally substituted with an alkyl group, an aryl group, an ester group, a carboxy group, an amide group, a cyano group, a nitro group, a halogen atom, an acyl group, $CF_3$, O (Continued)

$(CH_2)_jOCH_3$, a carbamate group, or an alkoxy group, each of $R^3$ and $R^4$ independently represents an alkyl group, an aryl group, an acyl group, an ester group, an alkylsulfonyl group, or an arylsulfonyl group, each of $R^5$ and $R^6$ independently represents a hydrogen atom, an alkyl group having from 1 to 20 carbon atoms, or an aryl group, and $n+m \geq 1$.

5 Claims, 2 Drawing Sheets

(51) Int. Cl.
| | |
|---|---|
| B01D 53/62 | (2006.01) |
| B01D 53/80 | (2006.01) |
| B01D 53/96 | (2006.01) |
| B01J 20/22 | (2006.01) |
| B01J 20/34 | (2006.01) |

(56) References Cited

OTHER PUBLICATIONS

Zhu et al., "Reversible tuning of pore size and CO2 adsorption in azobenzene functionalized porous organic polymers." Chem. Sci. 2014, 5, 4957-4961.*
Mar. 24, 2022 (EP) Extended European Search Report Application No. 20763430.4.
Smith et al. "A novel structural class of photoswitchable oligonucleotide" Tetrahedron Letters 48 (2007) 6569-6572.
Cheng et al. "Reversible Laser-Induced Bending of Pseudorotaxane Crystals", J. Am. Chem. Soc. 2018, 140, 90-93.
Ruck-Braun et al. "Azobenzene-Based w-Amino Acids and Related Building Blocks: Synthesis, Properties, and Application in Peptide Chemistry", Synthesis 2009, No. 24, 99 4256-4267.
Shinmori et al. "A novel light-gated sugar receptor, which shows high glucose selectivity". J, Chem Soc. Perkin Trans. 2, 1998, 847-852.
Brancatelli et al. "Reversible Molecular Motion of a Biscalix[5]arene Host Driven by a Photoresponsive Guest", Chem. Asian J. 2012, 7, 50-54.
Cheng et al. "Controllable Adsorption of CO2 on Smart Adsorbents: An Interplay between Amines and Photoresponsive Molecules". Chem. Mater. 2018, 30, 3429?3437.
Lien et al. "Photomodulated Blocking of Gramicidio Ion Channels" J. Am. Chem. Soc., 1996, 118, 12222-12223.
Lee et al. "Catalytic Turnover of Substrate Benzylamines by the Quinone-Dependent Plasma Amine Oxidase Leads to H2O2-Dependent Inactivation: Evidence for Generation of a Cofactor-Derived Benzoxazole" Biochemistry 2001, 40, 822-829.
Hubbard et al. "Pole Polymeric Nonlinear Optical Materials, Enhanced Second Harmonic Generation Temporal Stability of Epoxy: Based Matrices Containing a Difunctional Chromophoric Co-Monomer". Chem. Mater., 1992, 4, 965-968.
Cattani-Scholz et al. "Photoresponsive Dendritic Azobenzene Peptides". Chembiochem 2001, 2, 542-549.
Pearson et al. "Photoswitch inhibitors of a-chymotrypsin-increased substitution and peptidic character in peptidomimetic boronate esters". Org. Biomol. Chem. 2006, 4, 3618-3628.
Kamenjicki et al. "Photoresponsive Azobenzene Photonic Crystals". J, Phys. Chem. B 2004, 108, 12637-12639.
Zeyat et al. "Building photoswitchable 3,4'-AMPB petides: Probing chemical ligation methods with reducible azobenzes thioesters". Beilstein Journal of Organic Chemistry, 2012, 8, 890-896.

* cited by examiner

COMPOUND, CARBON DIOXIDE ABSORPTION/RELEASE AGENT, CARBON DIOXIDE COLLECTION METHOD, AND CARBON DIOXIDE COLLECTION APPARATUS

CROSS-REFERENCE TO RELATED APPLICATIONS

This application is a National Stage Application under 35 U.S.C. 371 of co-pending PCT application number PCT/JP2020/008552 designating the United States and filed Feb. 28, 2020, which claims the benefit of JP application number 2019-036824 and filed Feb. 28, 2019, each of which are hereby incorporated by reference in their entireties.

TECHNICAL FIELD

The present disclosure relates to a novel compound, a carbon dioxide absorption/release agent containing the novel compound, a method of collecting carbon dioxide using the same, and a carbon dioxide collection apparatus.

BACKGROUND ART

Global warming has recently progressed, and many global disasters have been caused due to climate change. Under such circumstances, reduction of greenhouse gases that would serve as a warming factor, in particular, reduction of carbon dioxide having a large impact, has been taken up as an international commitment in the International Conference of the Parties to the United Nations Framework Convention on Climate Change (COP), and efforts to reduce carbon dioxide emissions have been made earnestly on a global scale. However, it has been difficult to achieve the reduction targets. Therefore, a technique for collecting and storing emitted carbon dioxide instead of reducing carbon dioxide emissions have become important. Gas absorbents for directly collecting carbon dioxide from carbon dioxide generation sources and collection and storage systems using such gas absorbents have been actively studied, and development of some of these has advanced to a validation phase.

For example, WO 2009/001804A mentions that, as a chemical absorption technique, an aqueous solution containing isopropylaminoethanol and piperazine is used, and heating the solution after absorption of carbon dioxide to 70° C. or higher enables carbon dioxide to be released.

The most part of carbon dioxide to be emitted is finally emitted by use of fossil carbon resources as fuel or chemical raw material. Since the Industrial Revolution, enormous fossil carbon resources have been continuously used, and thus carbon dioxide in the atmosphere has continued to increase significantly. Additionally, there has been a concern about depletion of fossil carbon resources. In addition to reduction of carbon dioxide in order to prevent global warming, techniques of taking carbon dioxide, which is final waste of carbon resources, as a carbon resource and converting carbon dioxide into a substance that can be used as fuel or chemical raw material have been required. Research and development on such techniques have been recently advanced.

In order to practice a technique of collecting and storing carbon dioxide and utilizing the carbon dioxide as a carbon resource, it is necessary to make each of steps of collecting and storing carbon dioxide and of emitting the collected carbon dioxide a step in which no carbon dioxide is emitted and to establish the technique as a technique that does augment carbon dioxide, but use of energy in each step may be problematic. The step of collecting or releasing carbon dioxide usually requires an operation such as heating or pressure reduction. In a case in which energy including energy derived from fossil fuel such as electric power is used, carbon dioxide is indirectly emitted.

For development of collection/release technique of carbon dioxide without emission of carbon dioxide, techniques of using light energy, which is renewable energy, have been developed. Use of renewable energy enables indirect carbon dioxide emissions to be avoided. For example, in Japanese National-Phase Publication (JP-A) No. 2015-529550, a gas absorption/release technique using light energy has been achieved by combining a technique of gas physical adsorption via a porous metal organic framework (MOF) with a photostructural conversion of MOF-constituting organic molecules. A MOF is a three-dimensional crystalline porous material of an important type, which is composed of a central metal and organic ligands periodically bonded to form a crystalline and porous arrangement, and can trap gases (hydrogen, carbon dioxide, and methane). The MOF also releases gas from the inside of the pores by a change in the optical structure due to ultraviolet light irradiation and then can be regenerated.

In Chem. Mater. 2018, 30, 3429-3437, a carbon dioxide collection/release technique using light energy has been achieved by combining a solid-phase amine absorbent of carbon dioxide (mesoporous silica-supported amine carbon dioxide absorbent) with azobenzene that converts its structure via ultraviolet light/visible light irradiation. The amine moiety is caused to absorb carbon dioxide, and a change in the optical structure of the azobenzene moiety in the vicinity of the amine moiety is induced via ultraviolet light irradiation so that carbon dioxide can be released. After carbon dioxide is released, carbon dioxide absorption is recovered by visible light irradiation.

SUMMARY OF INVENTION

Technical Problem

Toward reduction and recycling of carbon dioxide, development of collection/release techniques of carbon dioxide of collecting and storing carbon dioxide and releasing the collected carbon dioxide to convert the carbon dioxide into valuable chemical substances have been advanced, but development of a technique of not emitting carbon dioxide in each step has not been achieved.

A chemical absorption method of carbon dioxide as described in WO 2009/001804A generally has advantages in that the carbon dioxide adsorption rate is high and carbon dioxide is likely to be selectively captured even in a mixed gas. However, a heating step is required at the stage of releasing the absorbed carbon dioxide, and thus a load of new thermal energy supply for release is generated. In a case of supplying thermal energy via electric power, which generally includes power generation with fossil fuel, indirect carbon dioxide emission is involved. The thermal energy may be supplied by exhaust heat of a thermal power plant or the like, but places where the exhaust heat is available are limited.

As in JP-A No. 2015-529550 and Chem. Mater. 2018, 30, 3429-3437, techniques have also been developed, in which emission of carbon dioxide emission is suppressed not by using heat energy for release of carbon dioxide but by using light energy as renewable energy. However, in the method described in JP-A No. 2015-529550 using physical adsorption via a MOF, pressure control is required in the step of absorbing carbon dioxide, and carbon dioxide is emitted in the process of generating electric power for use in the pressure control. A physical adsorption method generally has a capacity of collecting carbon dioxide inferior to that of a chemical absorption method, and requires pressure control for adsorption of carbon dioxide. In addition, physical adsorption largely depends on the porous structure of a carrier. The fact that it is difficult to selectively capture a target gas from the gas flow although the gas flow can be captured is also a problem.

The method described in Chem. Mater. 2018, 30, 3429-3437 is a technique that achieves selective carbon dioxide absorption and combines chemical absorption of carbon dioxide by a solid amine absorbent and release of carbon dioxide by optical structure conversion in the vicinity of the carbon dioxide absorbent. In the technique, pressure control is performed for the carbon dioxide absorption, and electric power is required in the carbon dioxide collection process as in the physical adsorption method. Carbon dioxide is indirectly emitted due to power consumption.

Although carbon dioxide collection/release techniques using light energy, which is renewable energy, have been developed, such techniques, at the moment, include a step of using energy including energy derived from fossil carbon resources such as electric power, indirectly emitting carbon dioxide. Development of a technique of achieving collection and release of carbon dioxide under normal temperature and normal pressure without using energy derived from fossil fuel has not been accomplished.

An object of the present disclosure is to provide a novel compound.

Another object of the disclosure is to provide a carbon dioxide absorption/release agent having a low environmental load (e.g., using renewable energy at normal temperature and normal pressure) and capable of repeatedly absorbing and releasing carbon dioxide.

Another object of the disclosure is to provide a carbon dioxide collection method and a carbon dioxide collection apparatus having a low environmental load (e.g., using renewable energy at normal temperature and normal pressure) and capable of repeatedly absorbing and releasing carbon dioxide.

The absorption/release of carbon dioxide by the carbon dioxide absorption/release agent of the disclosure indicates chemical absorption/release. Here, the absorption of carbon dioxide refers to, for example, binding of carbon dioxide to the carbon dioxide absorption/release agent, and the release of carbon dioxide refers to, for example, breaking of the binding between carbon dioxide and the carbon dioxide absorption/release agent.

Solution to Problem

As a result of intensive studies in view of the above, the present inventors have found that subjecting a compound having a specific structure to light irradiation only or to light irradiation and room temperature heating conditions reversibly changes the structure to thereby enable the compound to repeatedly absorb/release carbon dioxide.

Specific means for solving the problem include the following aspects.

<1>

A compound represented by Formula (1):

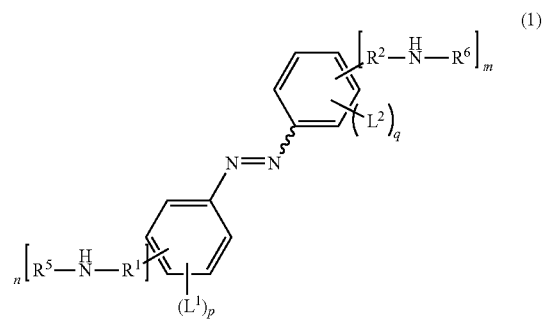

wherein, in Formula (1), each of $L^1$ and $L^2$ independently represents an alkyl group having from 1 to 20 carbon atoms, an alkoxy group having from 1 to 20 carbon atoms, $NH_2$, $NHR^3$, $NR^3R^4$, an ester group, a carboxy group, an amide group, a cyano group, a nitro group, a halogen atom, an acyl group, $CF_3$, $O(CH_2)_lOCH_3$, a carbamate group, or an aryl group, provided that l represents 1 or 2, each of p and q independently represents an integer from 0 to 4, each of $R^1$ and $R^2$ independently represents a divalent hydrocarbon group having from 1 to 10 carbon atoms, at least one hydrogen atom of the divalent hydrocarbon group is optionally substituted with an alkyl group, an aryl group, an ester group, a carboxy group, an amide group, a cyano group, a nitro group, a halogen atom, an acyl group, $CF_3$, $O(CH_2)_lOCH_3$, a carbamate group, or an alkoxy group, each of $R^3$ and $R^4$ independently represents an alkyl group, an aryl group, an acyl group, an ester group, an alkylsulfonyl group, or an arylsulfonyl group, each of $R^5$ and $R^6$ independently represents a hydrogen atom, an alkyl group having from 1 to 20 carbon atoms, or an aryl group, and each of n and m independently represents an integer from 0 to 5, provided that n+m≥1.

<2>

The compound according to <1>, the compound being at least one selected from the group consisting of the following Compound (1-1) to the following Compound (1-9):

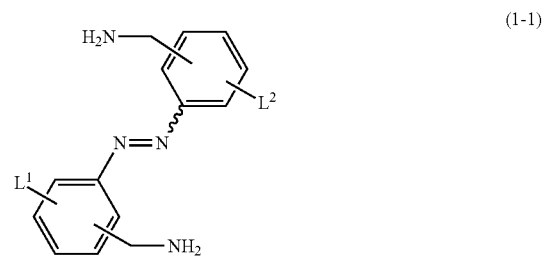

-continued (1-2)

(1-3)

(1-4)

(1-5)

(1-6)

(1-7)

(1-8)

(1-9)

wherein, in Compound (1-1) and Compound (1-9), each of $L^1$ and $L^2$ independently represents an alkyl group having from 1 to 6 carbon atoms, an alkoxy group having from 1 to 6 carbon atoms, $NH_2$, $NHR^3$, $NR^3R^4$, an ester group, a carboxy group, an amide group, a cyano group, a nitro group, a halogen atom, an acyl group, $CF_3$, $O(CH_2)_lOCH_3$, a carbamate group, or an aryl group, provided that $l$ represents 1 or 2, each of $R^3$ and $R^4$ independently represents an alkyl group, an aryl group, an acyl group, an ester group, an alkylsulfonyl group, or an arylsulfonyl group.

<3>

The compound according to <1>, the compound being at least one selected from the group consisting of the following Compound (2-1) to the following Compound (2-5):

(2-1)

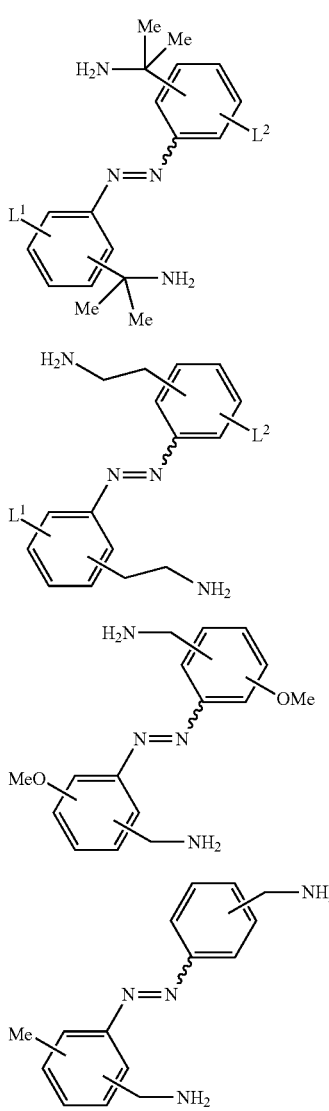

wherein, in Compound (2-1) to Compound (2-3), each of $L^1$ and $L^2$ independently represents an alkyl group having from 1 to 20 carbon atoms, an alkoxy group having from 1 to 20 carbon atoms, $NH_2$, $NHR^3$, $NR^3R^4$, an ester group, a carboxy group, an amide group, a cyano group, a nitro group, a halogen atom, an acyl group, $CF_3$, $O(CH_2)_lOCH_3$, a carbamate group, or an aryl group, provided that l represents 1 or 2, each of $R^3$ and $R^4$ independently represents an alkyl group, an aryl group, an acyl group, an ester group, an alkylsulfonyl group, or an arylsulfonyl group.

<4>
A carbon dioxide absorption/release agent comprising the compound according to any one of <1> to <3>.

<5>
A carbon dioxide collection method in which carbon dioxide is collected using the carbon dioxide absorption/release agent according to <4>.

<6>
The carbon dioxide collection method according to <5>, comprising a step of immersing the carbon dioxide absorption/release agent in a solvent, and a step of bringing a fluid containing carbon dioxide into contact with the carbon dioxide absorption/release agent after the immersion.

<7>
The carbon dioxide collection method according to <6>, further comprising a step of irradiating the carbon dioxide absorption/release agent with ultraviolet light having a wavelength of from 300 nm to 400 nm, sunlight, or simulated sunlight to release absorbed carbon dioxide from the carbon dioxide absorption/release agent.

<8>
The carbon dioxide collection method according to <7>, further comprising a step of irradiating the carbon dioxide absorption/release agent with visible light having a wavelength of from 400 nm to 570 nm or leaving the carbon dioxide absorption/release agent in a solution at room temperature for a certain period of time to bring the carbon dioxide absorption/release agent into a state in which it is capable of absorbing carbon dioxide.

<9>
The carbon dioxide collection method according to any one of <6> to <8>, wherein the solvent is at least one selected from the group consisting of chloroform, toluene, and acetonitrile.

<10>
A carbon dioxide collection apparatus, comprising:
the carbon dioxide absorption/release agent according to <4>; and
an irradiation device that irradiates the carbon dioxide absorption/release agent with at least one of sunlight, simulated sunlight, ultraviolet light having a wavelength of from 300 nm to 400 nm, or visible light having a wavelength of from 400 nm to 570 nm.

<11>
The carbon dioxide collection apparatus according to <10>, further comprising a supply device that supplies a fluid containing carbon dioxide to the carbon dioxide absorption/release agent.

Advantageous Effects of Invention

According to the present disclosure, it is possible to provide a novel compound.

According to another aspect of the disclosure, it is possible to provide a carbon dioxide absorption/release agent having a low environmental load (e.g., using renewable energy at normal temperature and normal pressure) and capable of repeatedly absorbing and releasing carbon dioxide.

According to another aspect of the disclosure, it is possible to provide a carbon dioxide collection method and a carbon dioxide collection apparatus having a low environmental load (e.g., using renewable energy at normal temperature and normal pressure) and capable of repeatedly absorbing and releasing carbon dioxide.

DESCRIPTION OF EMBODIMENTS

Figure 1:
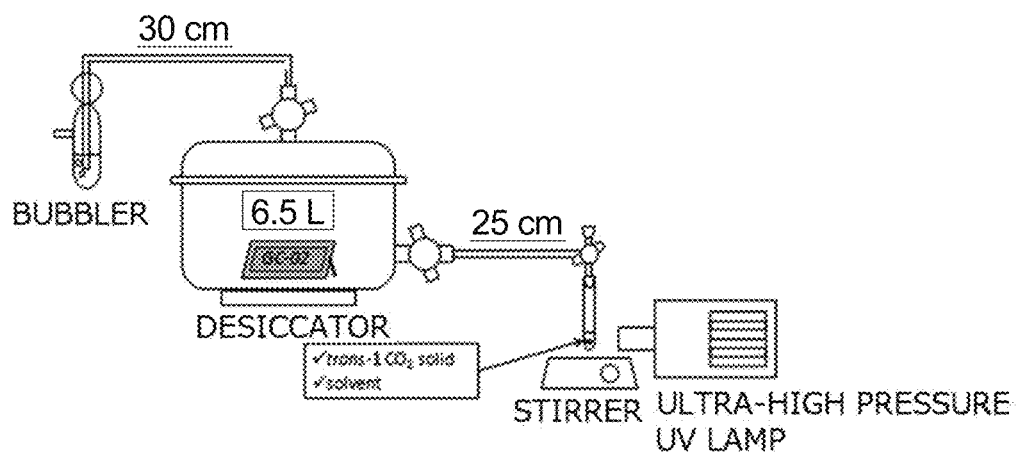
FIG. 1 is a schematic view of an apparatus for use in a non-dispersive infrared absorption method (NDIR).

Hereinafter, an embodiment as an example of the present invention will be described. The invention is not limited to the following embodiment at all, and can be implemented with, if appropriate, modifications within the scope of the object of the present disclosure.
[Compound]

The compound of the present disclosure consists of a compound represented by the following Formula (1).

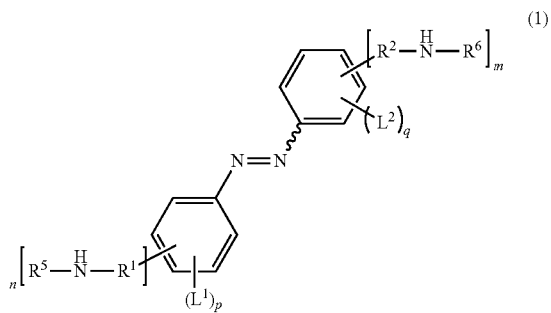

In Formula (1), each of $L^1$ and $L^2$ independently represents an alkyl group having from 1 to 20 carbon atoms, an alkoxy group having from 1 to 20 carbon atoms, $NH_2$, $NHR^3$, $NR^3R^4$, an ester group, a carboxy group, an amide group, a cyano group, a nitro group, a halogen atom, an acyl group, $CF_3$, $O(CH_2)_lOCH_3$, a carbamate group, or an aryl group, provided that l represents 1 or 2, each of p and q independently represents an integer from 0 to 4, each of $R^1$ and $R^2$ independently represents a divalent hydrocarbon group having from 1 to 10 carbon atoms, at least one hydrogen atom of the divalent hydrocarbon group is optionally substituted with an alkyl group, an aryl group, an ester group, a carboxy group, an amide group, a cyano group, a nitro group, a halogen atom, an acyl group, $CF_3$, $O(CH_2)_lOCH_3$, a carbamate group, or an alkoxy group, each of $R^3$ and $R^4$ independently represents an alkyl group, an aryl group, an acyl group, an ester group, an alkylsulfonyl group, or an arylsulfonyl group, each of $R^5$ and $R^6$ independently represents a hydrogen atom, an alkyl group having from 1 to 20 carbon atoms, or an aryl group, and each of n and m independently represents an integer from 0 to 5, provided that $n+m \geq 1$.

In Formula (1), the number of carbon atoms of the alkyl group having from 1 to 20 carbon atoms represented by $L^1$ or $L^2$ is preferably from 1 to 6, more preferably from 1 to 3, still more preferably 1 or 2, and particularly preferably 1.

In Formula (1), the number of carbon atoms of the alkoxy group having from 1 to 20 carbon atoms represented by $L^1$ or $L^2$ is preferably from 1 to 6, more preferably from 1 to 3, still more preferably 1 or 2, and particularly preferably 1.

In Formula (1), among $NH_2$ (amino group), $NHR^3$, and $NR^3R^4$ represented by $L^1$ or $L^2$, $NH_2$ (amino group) or $NHR^3$ is preferable, and $NH_2$ (amino group) is more preferable.

each of $R^3$ and $R^4$ is independently an alkyl group, an aryl group, an acyl group, an ester group, an alkylsulfonyl group, or an arylsulfonyl group. As the alkyl group, an alkyl group having from 1 to 6 carbon atoms is preferable, an alkyl group having from 1 to 3 carbon atoms is more preferable, an alkyl group having 1 or 2 carbon atoms is further preferable, and an alkyl group having 1 carbon atom is particularly preferable. As the aryl group, an aryl group having from 6 to 30 carbon atoms is preferable, and an aryl group having from 6 to 20 carbon atoms is more preferable. As the acyl group, an acyl group having from 1 to 6 carbon atoms is preferable, and an aryl group having from 1 to 3 carbon atoms is more preferable. As the ester group, an ester group having from 1 to 6 carbon atoms is preferable, and an ester group having from 1 to 3 carbon atoms is more preferable. As the alkylsulfonyl group, an alkylsulfonyl group having from 1 to 6 carbon atoms is preferable, an alkylsulfonyl group having from 1 to 3 carbon atoms is more preferable, an alkyl sulfonyl group having 1 or 2 carbon atoms is further preferable, and an alkylsulfonyl group having 1 carbon atom is particularly preferable. As the arylsulfonyl group, an arylsulfonyl group having from 6 to 30 carbon atoms is preferable, and an arylsulfonyl group having from 6 to 20 carbon atoms is more preferable.

In Formula (1), the number of carbon atoms of the ester group represented by $L^1$ or $L^2$ is preferably from 1 to 6 and more preferably from 1 to 3.

In Formula (1), the number of carbon atoms of the acyl group represented by $L^1$ or $L^2$ is preferably from 1 to 6 and more preferably from 1 to 3.

In Formula (1), 1 of $O(CH_2)_lOCH_3$ represented by $L^1$ or $L^2$ represents 1 or 2.

In Formula (1), as the aryl group represented by $L^1$ or $L^2$, an aryl group having 6 to 30 carbon atoms is preferable, and an aryl group having from 6 to 20 carbon atoms is more preferable.

In Formula (1), each of $L^1$ and $L^2$ is independently preferably an alkyl group having from 1 to 6 carbon atoms, an alkoxy group having from 1 to 6 carbon atoms, $NH_2$, $NHR^3$, $NR^3R^4$, an ester group, an amide group, a nitro group, a halogen atom, an acyl group, $CF_3$, $O(CH_2)_lOCH_3$, or an aryl group, more preferably an alkyl group having from 1 to 6 carbon atoms, an alkoxy group having from 1 to 6 carbon atoms, $NH_2$, $NHR^3$, or $NR^3R^4$, still more preferably an alkyl group having from 1 to 3 carbon atoms, and particularly preferably a methyl group.

In Formula (1), each of p and q independently represents preferably an integer from 0 to 3, more preferably an integer from 0 to 2, and still more preferably 0 or 1.

In Formula (1), each of $R^1$ and $R^2$ independently represents a divalent hydrocarbon group having from 1 to 10 carbon atoms, and at least one hydrogen atom of the divalent hydrocarbon group is optionally substituted with an alkyl group, an aryl group, an ester group, a carboxy group, an amide group, a cyano group, a nitro group, a halogen atom, an acyl group, $CF_3$, $O(CH_2)_lOCH_3$, a carbamate group, or an alkoxy group, is preferably an unsubstituted methylene group (—$CH_2$—) or an unsubstituted ethylene group (—$CH_2CH_2$—), and more preferably an unsubstituted methylene group.

In Formula (1), each of $R^5$ and $R^6$ is independently preferably a hydrogen atom or an alkyl group having from 1 to 3 carbon atoms, more preferably a hydrogen atom or an alkyl group having from 1 to 2 carbon atoms, and still more preferably a hydrogen atom or a methyl group.

In Formula (1), each of n and m independently preferably represents an integer from 0 to 3 and more preferably represent an integer from 0 to 2. The sum of n and m is preferably 4 or less.

Specific examples of the compound represented by Formula (1) include compounds represented by the following Formula (1-1) to the following Formula (1-9) (hereinafter, the compounds are each also referred to as Compound (1-1) to Compound (1-9)), but the compound represented by Formula (1) is not limited to these specific examples.

Among these, Compound (1-1), Compound (1-3), or Compound (1-8) is preferable, Compound (1-1) or Compound (1-3) is more preferable, and Compound (1-1) is particularly preferable.

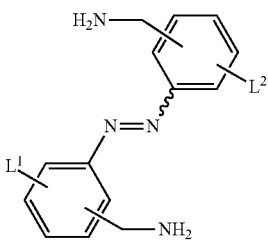

(1-1)

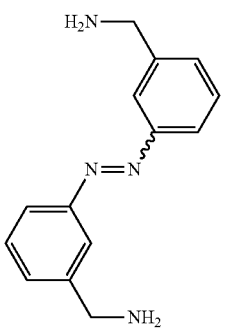

(1-2)

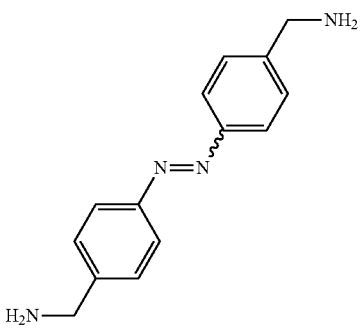

(1-3)

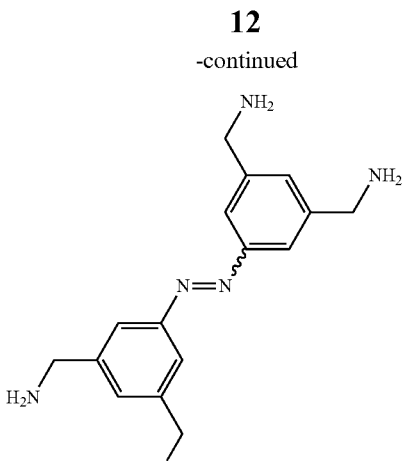

(1-4)

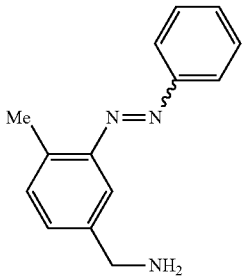

(1-5)

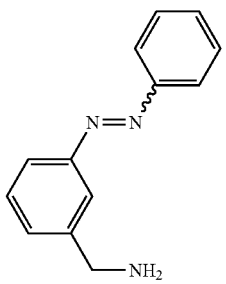

(1-6)

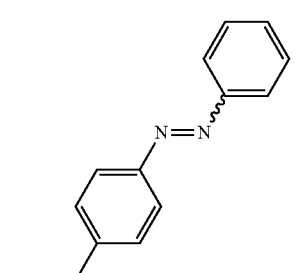

(1-7)

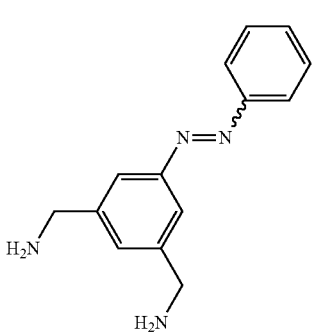

(1-8)

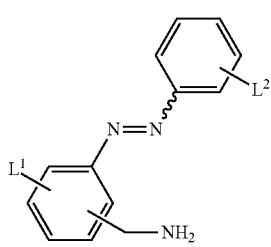
(1-9)

In Compound (1-1) and Compound (1-9), each of $L^1$ and $L^2$ independently represents an alkyl group having from 1 to 20 carbon atoms, an alkoxy group having from 1 to 20 carbon atoms, $NH_2$, $NHR^3$, $NR^3R^4$, an ester group, a carboxy group, an amide group, a cyano group, a nitro group, a halogen atom, an acyl group, $CF_3$, $O(CH_2)_lOCH_3$, a carbamate group, or an aryl group, provided that l represents 1 or 2, each of $R^3$ and $R^4$ independently represents an alkyl group, an aryl group, an acyl group, an ester group, an alkylsulfonyl group, or an arylsulfonyl group.

That is, $L^1$ and $L^2$ in Compound (1-1) and Compound (1-9) have the same meaning as $L^1$ and $L^2$ in Formula (1), and the same applies to preferred embodiments thereof.

Specific examples of the compound represented by Formula (1-1) include compounds represented by the following Formula (1-1-1) to the following Formula (1-1-9) (hereinafter, the compounds are each also referred to as Compound (1-1-1) to Compound (1-1-9)), but the compound represented by Formula (1-1) is not limited to these specific examples.

Among these, Compound (1-1-1), Compound (1-1-2), Compound (1-1-7), or Compound (1-1-8) is preferable, Compound (1-1-1) or Compound (1-1-2) is more preferable, and Compound (1-1-1) is particularly preferable.

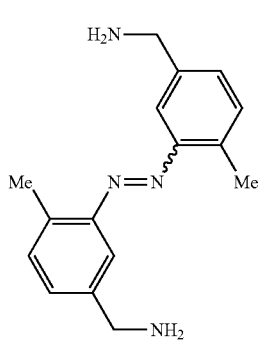
(1-1-1)

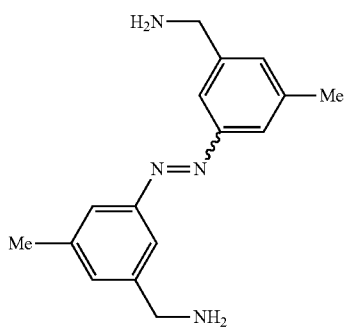
(1-1-2)

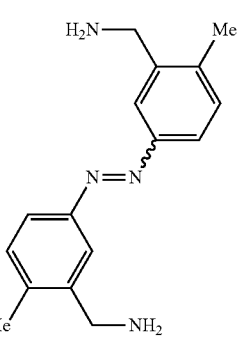
(1-1-3)

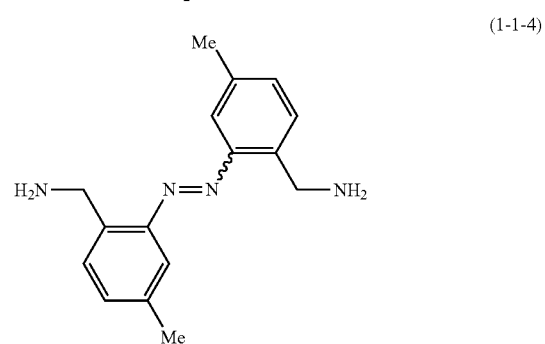
(1-1-4)

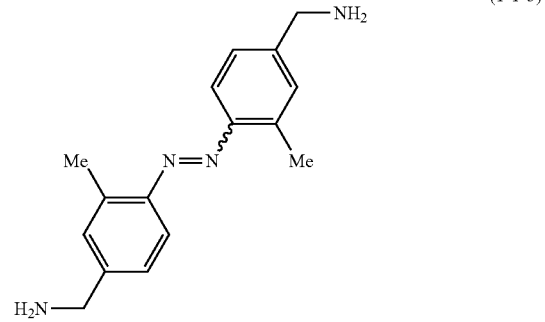
(1-1-5)

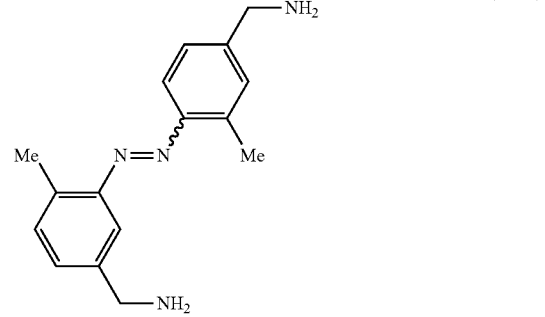
(1-1-6)

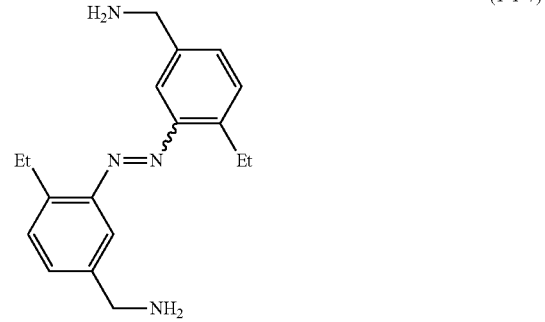
(1-1-7)

-continued

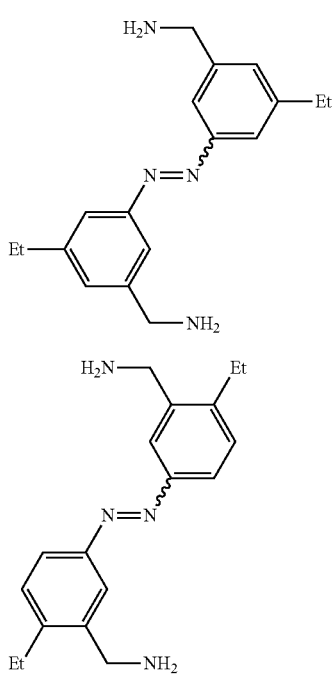
(1-1-8)

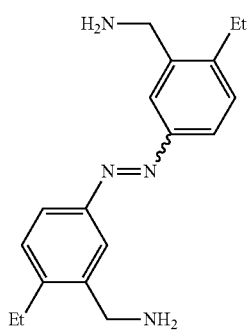
(1-1-9)

In Formula (1-1-1) to Formula (1-1-6), Me represents a methyl group. In Formula (1-1-7) to Formula (1-1-9), Et represents an ethyl group.

Specific examples of the compound represented by Formula (1-9) include compounds represented by the following Formula (1-9-1) to the following Formula (1-9-8) (hereinafter, the compounds are each also referred to as Compound (1-9-1) to Compound (1-9-8)), but the compound represented by Formula (1-9) is not limited to these specific examples.

Among these, Compound (1-9-1), Compound (1-9-2), Compound (1-9-4), or Compound (1-9-5) is preferable, Compound (1-9-1) or Compound (1-9-2) is more preferable, and Compound (1-9-1) is particularly preferable.

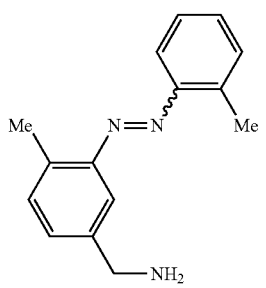
(1-9-1)

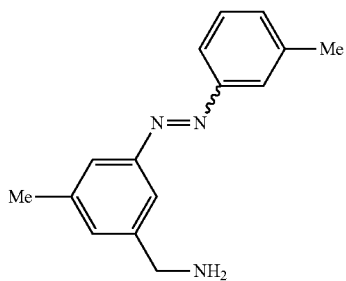
(1-9-2)

-continued

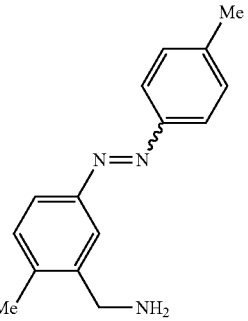
(1-9-3)

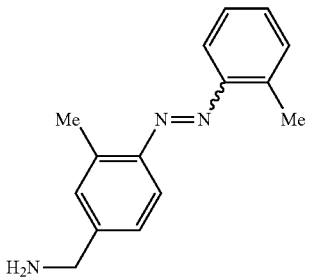
(1-9-4)

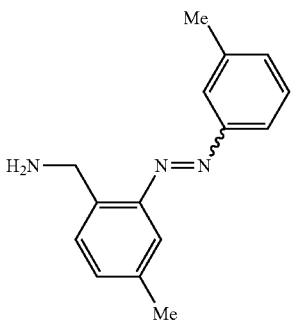
(1-9-5)

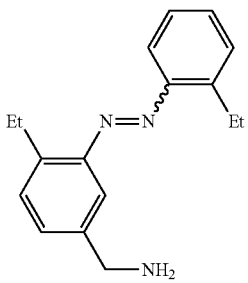
(1-9-6)

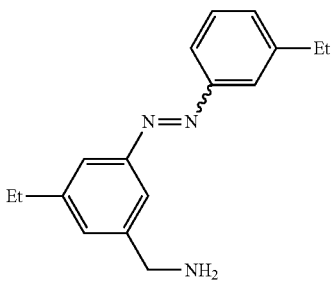
(1-9-7)

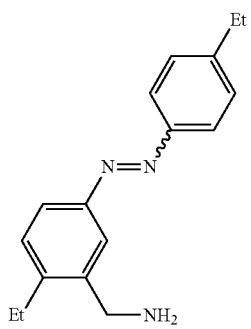
(1-9-8)

In Formula (1-9-1) to Formula (1-9-5), Me represents a methyl group. In Formula (1-9-6) to Formula (1-9-8), Et represents an ethyl group.

Furthermore, specific examples of the compound represented by Formula (1) include compounds represented by the following Formula (2-1) to the following Formula (2-5) (hereinafter, the compounds are each also referred to as Compound (2-1) to Compound (2-5)), but the compound represented by Formula (1) is not limited to these specific examples.

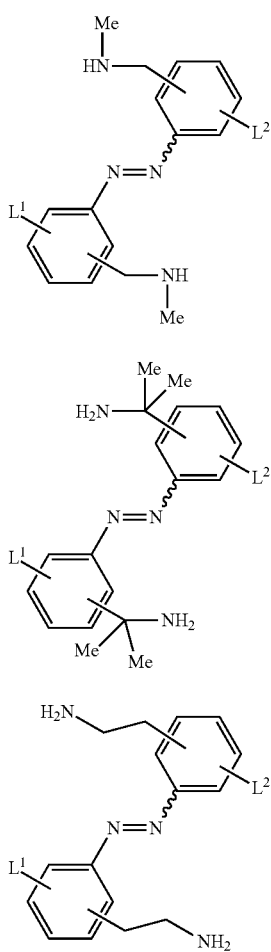

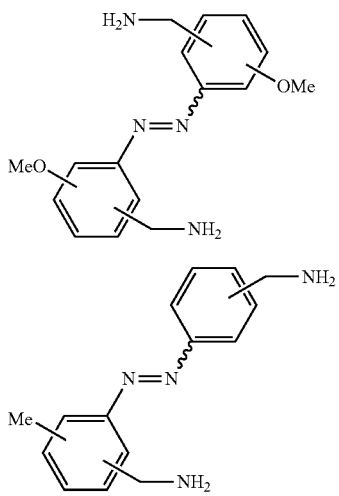

In Compound (2-1) to Compound (2-3), each of $L^1$ and $L^2$ independently represents an alkyl group having from 1 to 20 carbon atoms, an alkoxy group having from 1 to 20 carbon atoms, $NH_2$, $NHR^3$, $NR^3R^4$, an ester group, a carboxy group, an amide group, a cyano group, a nitro group, a halogen atom, an acyl group, $CF_3$, $O(CH_2)_lOCH_3$, a carbamate group, or an aryl group, provided that l represents 1 or 2, each of $R^3$ and $R^4$ independently represents an alkyl group, an aryl group, an acyl group, an ester group, an alkylsulfonyl group, or an arylsulfonyl group.

That is, $L^1$ and $L^2$ in Compound (2-1) to Compound (2-3) have the same meaning as $L^1$ and $L^2$ in Formula (1), and the same applies to preferred embodiments thereof.

Specific examples of the compound represented by Formula (2-1) include compounds represented by the following Formula (2-1-1) to the following Formula (2-1-9) (hereinafter, the compounds are each also referred to as Compound (2-1-1) to Compound (2-1-9)), but the compound represented by Formula (2-1) is not limited to these specific examples.

Among these, Compound (2-1-1), Compound (2-1-2), Compound (2-1-7), or Compound (2-1-8) is preferable, Compound (2-1-1) or Compound (2-1-2) is more preferable, and Compound (2-1-1) is particularly preferable.

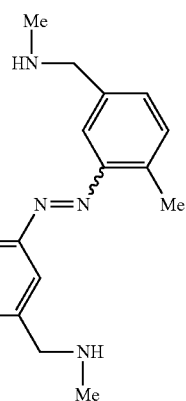
(2-1-1)

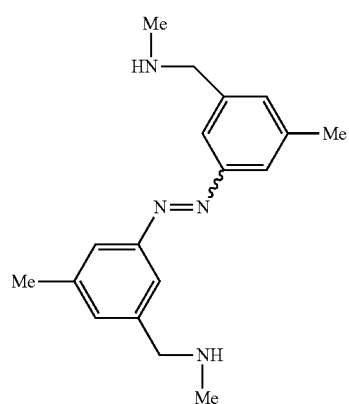
(2-1-2)
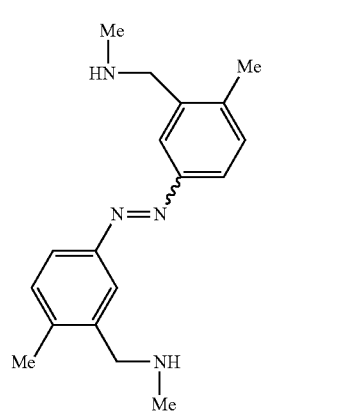
(2-1-3)
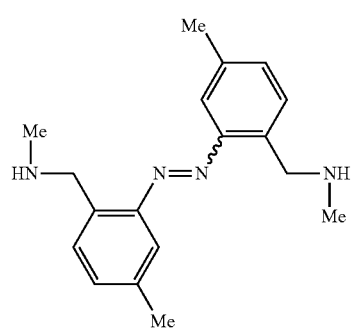
(2-1-4)
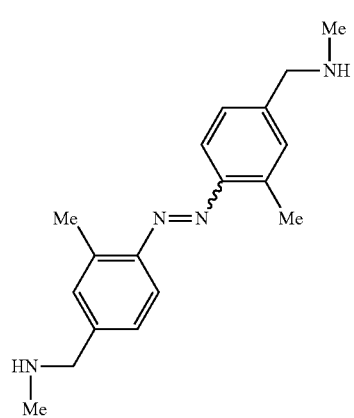
(2-1-5)
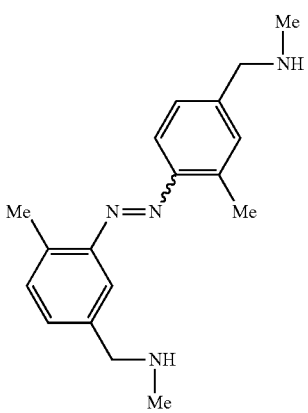
(2-1-6)
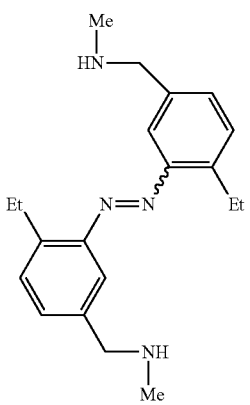
(2-1-7)
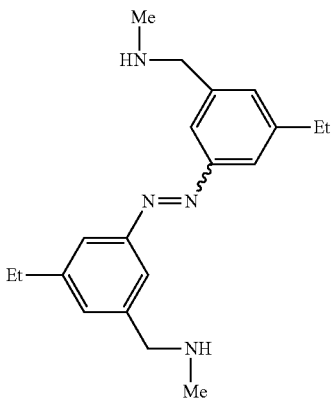
(2-1-8)
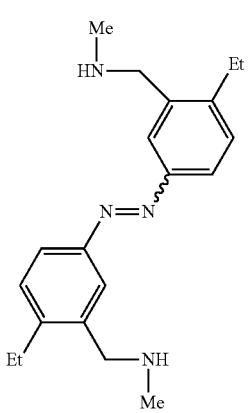
(2-1-9)

In Formula (2-1-1) to Formula (2-1-6), Me represents a methyl group. In Formula (2-1-7) to Formula (2-1-9), Et represents an ethyl group.

Specific examples of the compound represented by Formula (2-2) include compounds represented by the following Formula (2-2-1) to the following Formula (2-2-9) (hereinafter, the compounds are each also referred to as Compound (2-2-1) to Compound (2-2-9)), but the compound represented by Formula (2-2) is not limited to these specific examples.

Among these, Compound (2-2-1), Compound (2-2-2), Compound (2-2-7), or Compound (2-2-8) is preferable, Compound (2-2-1) or Compound (2-2-2) is more preferable, and Compound (2-2-1) is particularly preferable.

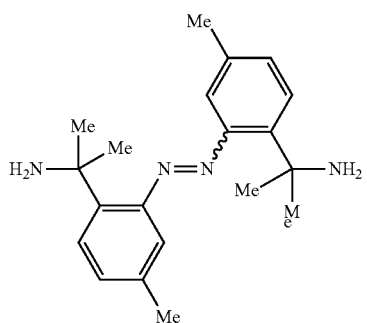
(2-2-4)

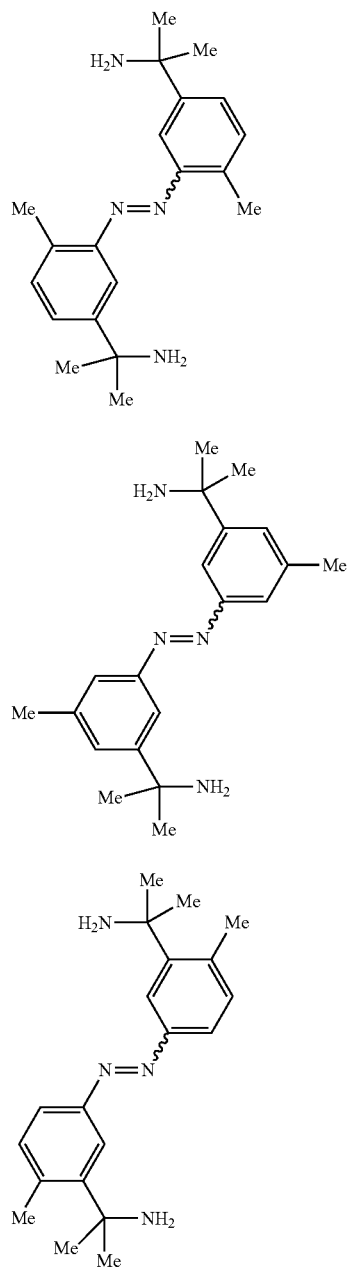
(2-2-1)

(2-2-2)

(2-2-3)

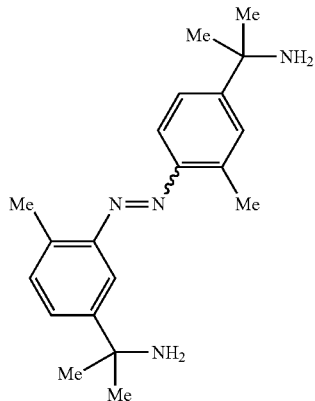
(2-2-5)

(2-2-6)

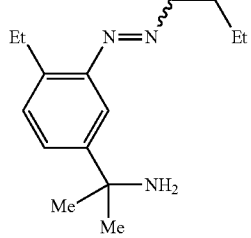
(2-2-7)

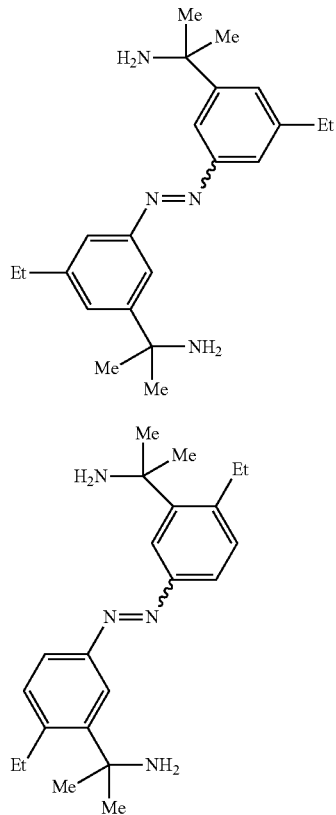

(2-2-8)

(2-2-9)

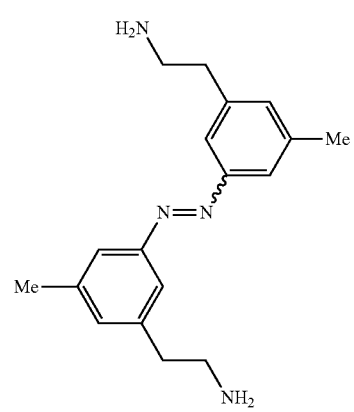

(2-3-2)

(2-3-3)

In Formula (2-2-1) to Formula (2-2-6), Me represents a methyl group. In Formula (2-2-7) to Formula (2-2-9), Et represents an ethyl group.

Specific examples of the compound represented by Formula (2-3) include compounds represented by the following Formula (2-3-1) to the following Formula (2-3-9) (hereinafter, the compounds are each also referred to as Compound (2-3-1) to Compound (2-3-9)), but the compound represented by Formula (2-3) is not limited to these specific examples.

Among these, Compound (2-3-1), Compound (2-3-2), Compound (2-3-7), or Compound (2-3-8) is preferable, Compound (2-3-1) or Compound (2-3-2) is more preferable, and Compound (2-3-1) is particularly preferable.

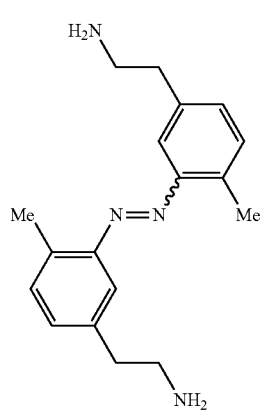

(2-3-1)

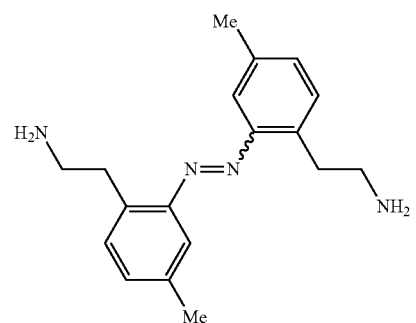

(2-3-4)

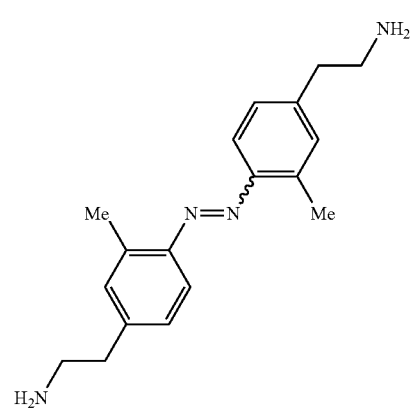

(2-3-5)

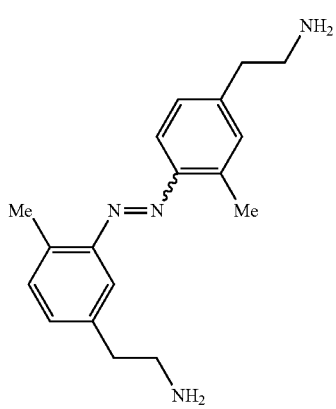
(2-3-6)

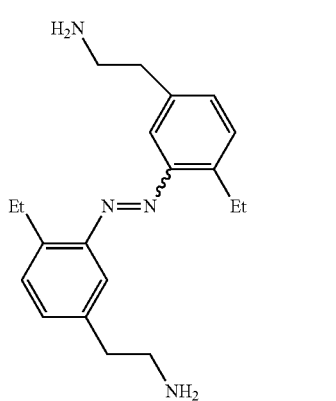
(2-3-7)

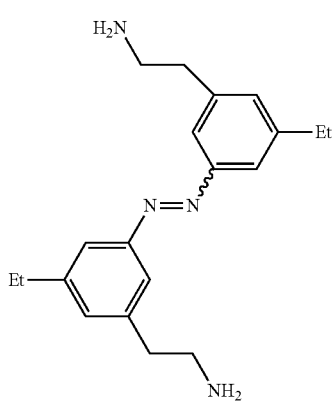
(2-3-8)

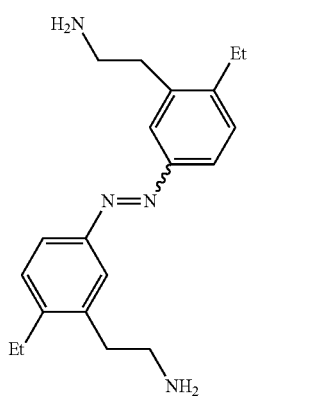
(2-3-9)

In the Formula (2-3-1) to Formula (2-3-6), Me represents a methyl group. In the Formula (2-3-7) to Formula (2-3-9), Et represents an ethyl group.

Specific examples of the compound represented by Formula (2-4) include compounds represented by the following Formula (2-4-1) to the following Formula (2-4-6) (hereinafter, the compounds are each also referred to as Compound (2-4-1) to Compound (2-4-6)), but the compound represented by Formula (2-4) is not limited to these specific examples.

Among these, Compound (2-4-1), Compound (2-4-2), Compound (2-4-5), or Compound (2-4-6) is preferable, Compound (2-4-1) or Compound (2-4-2) is more preferable, and Compound (2-4-1) is particularly preferable.

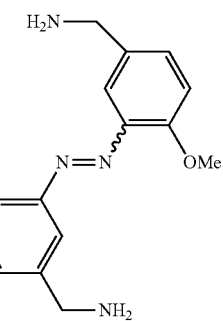
(2-4-1)

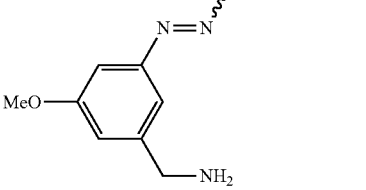
(2-4-2)

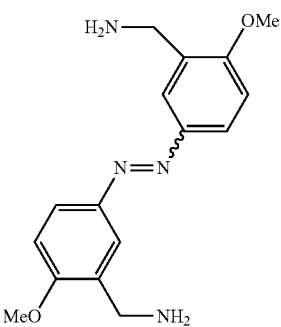
(2-4-3)

(2-4-4)
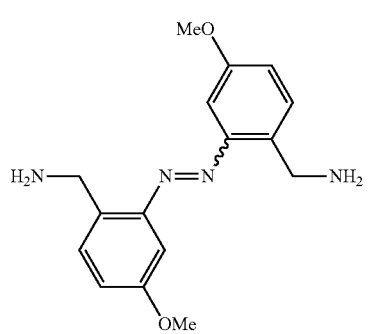

(2-5-1)
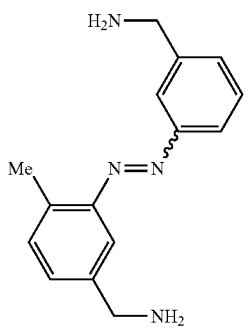

(2-4-5)
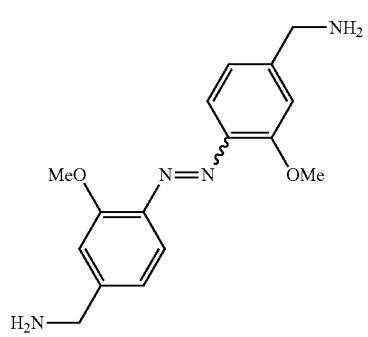

(2-5-2)
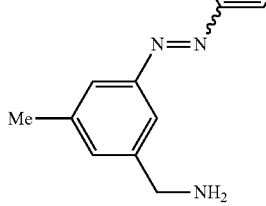

(2-5-3)

(2-4-6)
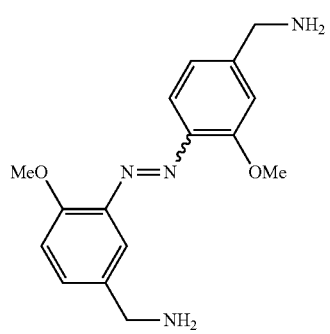

(2-5-4)
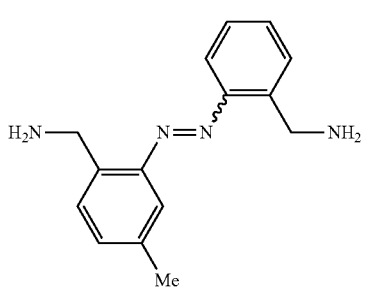

In the Formula (2-4-1) to Formula (2-4-6), OMe represents a methoxy group.

Specific examples of the compound represented by Formula (2-5) include compounds represented by the following Formula (2-5-1) to the following Formula (2-5-6) (hereinafter, the compounds are each also referred to as Compound (2-5-1) to Compound (2-5-6)), but the compound represented by Formula (2-5) is not limited to these specific examples.

Among these, Compound (2-5-1), Compound (2-5-2), Compound (2-5-5), or Compound (2-5-6) is preferable, Compound (2-5-1) or Compound (2-5-6) is more preferable, and Compound (2-5-6) is particularly preferable.

(2-5-5)
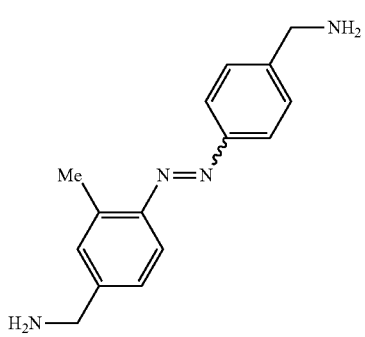

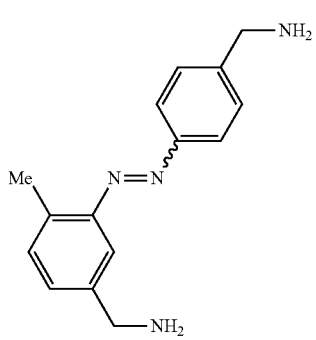

(2-5-6)

In the Formula (2-5-1) to Formula (2-5-6), Me represents a methyl group.

The compound represented by Formula (1) can be synthesized by, for example, conducting an azo coupling reaction and functional group conversion (reduction of ester followed by Mitsunobu reaction, deprotection), using methyl 3-amino-4-methylbenzoate as a starting material.

[Carbon Dioxide Absorption/Release Agent]

The carbon dioxide absorption/release agent of the present disclosure contains a compound represented by the above Formula (1) (hereinafter, also referred to as "Compound (1)"). With this configuration, it is possible to provide a carbon dioxide absorption/release agent having a low environmental load (e.g., using renewable energy at normal temperature and normal pressure) and capable of being repeatedly used. The carbon dioxide absorption/release agent of the disclosure has been found by the following findings.

A structure of the compound of the disclosure is reversibly changed by light irradiation (visible light irradiation and ultraviolet light irradiation). The structure of the compound of the disclosure is reversibly changed by a combination of light irradiation (ultraviolet light irradiation) and heat at about room temperature. Specifically, it is considered that, when Compound (1) as a trans-azobenzene form is irradiated with ultraviolet light, Compound (1) changes to a cis-azobenzene form, and then when Compound (1) as the cis-azobenzene form is irradiated with visible light, Compound (1) changes to the trans-azobenzene form. It is considered that the isomerization of the cis-azobenzene form to the trans-azobenzene form is also changed by leaving the cis-azobenzene in a solution at a temperature of about room temperature. Examples of the solution in this case include methanol.

By utilizing this change in the molecular structure, a compound has been developed which changes affinity to carbon dioxide with renewable energy (light energy) having a low environmental load without the need of energy having a high environmental load such as high temperature thermal energy that has been conventionally used.

In particular, the molecular structure of Compound (1), adjusted by irradiation with visible light or being left in a solution (methanol) at room temperature, efficiently absorbs carbon dioxide in a solvent (chloroform) to give a storable solid. The solid is, for example, precipitated in a solvent as a storable solid. It is considered that irradiating this solid or a suspension thereof (chloroform solvent) with ultraviolet light causes the solid to take a different structure (cis-azobenzene form), which dissolves in the solvent (chloroform) and releases carbon dioxide. The cis-azobenzene form is re-irradiated with visible light or left in a methanol solvent at room temperature to thereby become a structure that can absorb carbon dioxide (trans-azobenzene form).

Therefore, the carbon dioxide absorption/release agent of the disclosure can be repeatedly accomplish absorption and release of carbon dioxide by adding only light energy, which is renewable energy.

(Application)

The carbon dioxide absorption/release agent of the present disclosure can be used in any situation where carbon dioxide is required or not required.

The carbon dioxide absorption/release agent of the disclosure can be transported as a solid while absorbing carbon dioxide. Thus, the carbon dioxide absorption/release agent can be moved to an arbitrary place to increase variations of utilization such as utilization of dispersed small amounts or utilization of a centralized large amount. For example, it is possible to supply carbon dioxide to a place where carbon dioxide is required, such as a plastic greenhouse for cultivating crops.

[Carbon Dioxide Collection Method]

The carbon dioxide collection method of the present disclosure collects carbon dioxide using the carbon dioxide absorption/release agent described above. The carbon dioxide collection method of the disclosure has a low environmental load and can repeatedly absorb and release carbon dioxide.

Specifically, the carbon dioxide collection method of the disclosure preferably includes the following steps:

1) a step of immersing the carbon dioxide absorption/release agent in a solvent (hereinafter, also referred to as "Step 1");
2) a step of bringing a fluid containing carbon dioxide into contact with the carbon dioxide absorption/release agent after the immersion (hereinafter, also referred to as "Step 2");
3) a step of irradiating the carbon dioxide absorption/release agent with ultraviolet light having a wavelength of from 300 nm to 400 nm, sunlight, or simulated sunlight after the above Step 2 to release the absorbed carbon dioxide from the carbon dioxide absorption/release agent (hereinafter, also referred to as "Step 3"); and
4) a step of irradiating the carbon dioxide absorption/release agent with visible light having a wavelength of from 400 nm to 570 nm or leaving the carbon dioxide absorption/release agent in a solution at room temperature for a certain period of time after the above Step 3 to bring the carbon dioxide absorption/release agent into a state capable of absorbing carbon dioxide (hereinafter, also referred to as "Step 4").

The method may include, before Step 1, a step of adjusting the carbon dioxide absorption/release agent by irradiating the carbon dioxide absorption/release agent with visible light or leaving the carbon dioxide absorption/release agent in a solution at room temperature for a certain period of time in order to allow the carbon dioxide absorption/release agent to absorb carbon dioxide.

The solvent used in Step 1 is not particularly limited.

The solvent is preferably at least one selected from the group consisting of chloroform, toluene, and acetonitrile, and particularly preferably chloroform.

In Step 2, bringing the fluid containing carbon dioxide into contact with the carbon dioxide absorption/release agent after the immersion in the solvent enables carbon dioxide to be absorbed by the carbon dioxide absorption/release agent. The method of bringing the fluid into contact with the carbon dioxide absorption/release agent is not particularly limited, and the fluid can be brought into contact with the carbon dioxide absorption/release agent by a known method.

In addition, a step of storing carbon dioxide in a state of being absorbed by the carbon dioxide absorption/release agent may be included between Step 2 and Step 3. A mode of storage is not particularly limited, and it is also possible to dry the carbon dioxide absorption/release agent that has absorbed carbon dioxide and then store the carbon dioxide absorption/release agent in a container at normal temperature.

In Step 3, the carbon dioxide absorption/release agent is irradiated with ultraviolet light having a wavelength of from 300 nm to 400 nm, sunlight, or simulated sunlight. It is considered that irradiation of ultraviolet light having a wavelength of from 300 nm to 400 nm, sunlight, or simulated sunlight changes the structure of the carbon dioxide absorption/release agent that has absorbed carbon dioxide to cause the absorbed carbon dioxide to be released. The absorbed carbon dioxide is preferably released from the carbon dioxide absorption/release agent by irradiation with sunlight, which is renewable energy that does not emit carbon dioxide.

Step 3 may further include a step of recovering carbon dioxide released from the carbon dioxide absorption/release agent. The carbon dioxide can be recovered by a known method.

In Step 4, the carbon dioxide absorption/release agent is irradiated with visible light having a wavelength of from 400 nm to 570 nm or left in a solution at room temperature for a certain period of time. Irradiating the carbon dioxide absorption/release agent with visible light having a wavelength of from 400 nm to 570 nm or leaving the carbon dioxide absorption/release agent in a solution at room temperature for a certain period of time changes the structure of the carbon dioxide absorption/release agent to thereby bring the carbon dioxide absorption/release agent into a state capable of absorbing carbon dioxide again.

The solution used in Step 4 is not particularly limited. Examples of the solution include methanol.

The room temperature indicates 25° C. When the carbon dioxide absorption/release agent is left at room temperature for a certain period of time, the agent is preferably left for 1 minute or more and 24 hours or less and more preferably left for 30 minutes or more and 5 hours or less.

[Carbon Dioxide Collection Apparatus]

The carbon dioxide collection apparatus of the present disclosure includes the carbon dioxide absorption/release agent described above, and an irradiation device that irradiates the carbon dioxide absorption/release agent with at least one of sunlight, simulated sunlight, ultraviolet light having a wavelength of from 300 nm to 400 nm, or visible light having a wavelength of from 400 nm to 570 nm.

The carbon dioxide collection apparatus may include a supply device that supplies a fluid containing carbon dioxide to the carbon dioxide absorption/release agent, may include a storage equipment that stores the carbon dioxide absorption/release agent in a state of including carbon dioxide absorbed, and may further include a recovery device for recovering carbon dioxide from the carbon dioxide absorption/release agent that has absorbed carbon dioxide.

Each device included in the carbon dioxide collection apparatus can be provided with a detection device for detecting carbon dioxide. The form of the detection device is not particularly limited as long as the detection device can detect carbon dioxide, and examples thereof include a carbon dioxide concentration meter by gas chromatography or a non-dispersive infrared absorption method.

The simulated sunlight is one of light sources and also referred to as a solar simulator. The spectrum of simulated sunlight is equivalent to that of sunlight outdoors in good weather.

The carbon dioxide collection apparatus of the disclosure uses renewable energy, and thus has a low environmental load and can repeatedly absorb and release carbon dioxide.

The supply device for supplying a fluid containing carbon dioxide is for bringing the fluid into contact with the carbon dioxide absorption/release agent. The supply device is not particularly limited as long as the device can supply the fluid so that the fluid may come into contact with the carbon dioxide absorption/release agent, and examples thereof include a pump and an air compressor.

The aspect of the irradiation device that irradiates the carbon dioxide absorption/release agent with at least one of sunlight, simulated sunlight, ultraviolet light having a wavelength of from 300 nm to 400 nm, or visible light having a wavelength of from 400 nm to 570 nm is not particularly limited as long as the irradiation device can irradiate the carbon dioxide absorption/release agent with light. Examples thereof include a carbon arc lamp, a mercury vapor arc lamp, an ultra-high pressure mercury lamp, a high pressure mercury lamp and a xenon lamp, a metal hydride lamp, a light emitting diode (LED), and sunlight. The irradiation device may be either a single irradiation device or plural irradiation devices. An irradiation device capable of irradiating all of simulated sunlight, ultraviolet light, and visible light may be used. As the irradiation device, a simulated sunlight irradiation device, an ultraviolet irradiation device, and a visible light irradiation device may be used in combination.

Examples of the device that emits sunlight includes a light collection opening capable of taking in sunlight. The aspect of the device is not particularly limited as long as the device can take in sunlight and irradiate the carbon dioxide absorption/release agent with the sunlight.

The storage equipment for storing the carbon dioxide absorption/release agent is equipment that stores the carbon dioxide absorption/release agent in a state where the carbon dioxide remains absorbed by the carbon dioxide absorption/release agent, and an aspect thereof is not particularly limited. The place where the carbon dioxide has been absorbed may be used as the storage equipment. The storage equipment may be provided at any place where the carbon dioxide absorption/release agent can be transported.

The carbon dioxide absorption/release agent that has absorbed carbon dioxide may be stored in a solid state after being filtered, and is preferably stored in a solid state. That is, from the viewpoint of improving storage efficiency, storage equipment fitted with a filtration device that enables storage of the carbon dioxide absorption/release agent in a solid state is preferable as the storage device.

The recovery device for recovering carbon dioxide from the carbon dioxide absorption/release agent that has absorbed carbon dioxide is for recovering carbon dioxide released from the carbon dioxide absorption/release agent, and an aspect thereof is not particularly limited.

Figure 4:
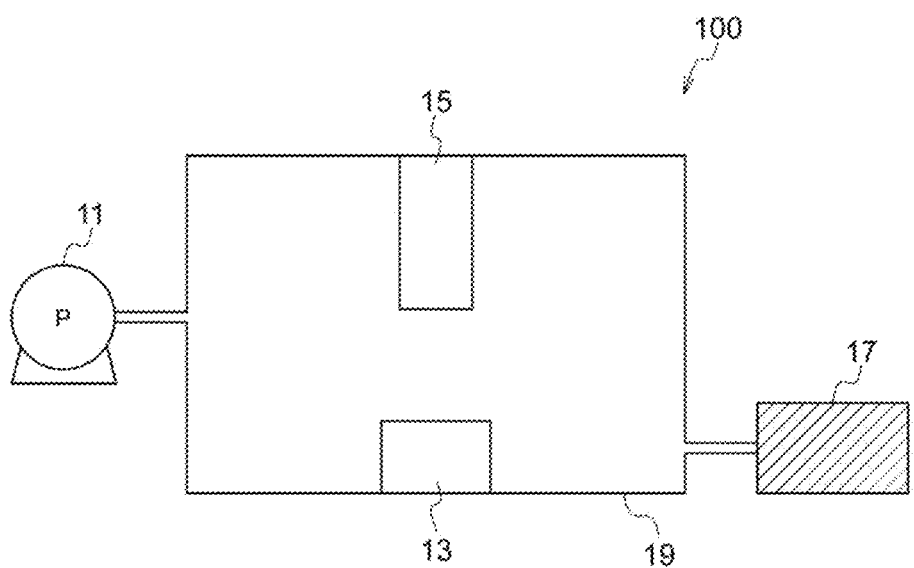
FIG. 4 is a carbon dioxide collection apparatus as an example of the present embodiment.

Hereinafter, an example of the carbon dioxide collection apparatus of the present embodiment is shown in FIG. 4.

A carbon dioxide collection apparatus 100 shown in FIG. 4 includes a supply device 11, a carbon dioxide absorption/release agent-containing container 13, an irradiation device 15, and a recovery device 17.

The supply device 11 can supply a fluid containing carbon dioxide into an environment chamber 19. In the carbon dioxide absorption/release agent-containing container 13, a carbon dioxide absorption/release agent and a solvent are accommodated.

The irradiation device 15 is a device that can switch among ultraviolet light and visible light, sunlight, or simulated sunlight to as necessary to emit the light. The recovery device 17 is a device for recovering carbon dioxide released from the carbon dioxide absorption/release agent.

In the carbon dioxide collection apparatus 100, when the fluid containing carbon dioxide is supplied from the supply device 11 into the environment chamber 19, the carbon dioxide absorption/release agent selectively absorbs carbon dioxide. Since the carbon dioxide absorbed by the carbon dioxide absorption/release agent can be stored, the carbon dioxide may be stored as it is in the carbon dioxide absorption/release agent-containing container 13 or may be transported to and stored in another storage equipment (not shown). The carbon dioxide absorption/release agent that has absorbed carbon dioxide may be stored in a solid state after being filtered.

Next, when ultraviolet light is emitted from the irradiation device 15 toward the carbon dioxide absorption/release agent-containing container 13 (containing a suspension of the carbon dioxide absorption/release agent that has absorbed carbon dioxide) after absorbing carbon dioxide, carbon dioxide is released from the carbon dioxide absorption/release agent that has absorbed carbon dioxide in the carbon dioxide absorption/release agent-containing container 13 to the outside of the carbon dioxide absorption/release agent-containing container 13. The released carbon dioxide can be recovered by the recovery device 17. Then, when visible light is emitted from the irradiation device 15 toward the carbon dioxide absorption/release agent-containing container 13, the carbon dioxide absorption/release agent in the carbon dioxide absorption/release agent-containing container 13 returns to a state capable of absorbing carbon dioxide.

EXAMPLES

Hereinafter, an embodiment as an example of the present invention will be described more specifically with reference to Examples. However, these Examples do not limit the invention.

For example, regarding Compound (1-1-1) represented by the above formula, the trans-azobenzene form of Compound (1-1-1) is denoted by "trans (1-1-1)", and the cis-azobenzene form of Compound (1-1-1) is denoted by "cis (1-1-1)".

NMR spectra were measured on BRUKER Biospin-AVANCE DPX-400 (400 MHz) and BRUKER Biospin-AVANCE 400M (400 MHz) spectrometers. $^{13}$C-NMR spectra were recorded using broadband proton decoupling. The remaining CHCl$_3$ peak or tetramethylsilane was used as an internal standard for $^1$H- and $^{13}$C-NMR in CDCl$_3$. Chemical shifts are expressed in δ (ppm) values and binding constants are expressed in Hertz (Hz).

The following abbreviations are used: s=singlet, d=doublet, m=multiplet, br s=broad singlet, and dd=double-doublet.

Example 1

The compound of the present disclosure (also referred to as "Compound (1-1-1)") was obtained according to the following synthesis route. The following synthesis route indicates a synthesis route for finally obtaining Compound (1-1-1) using Compound (2) as a starting material.

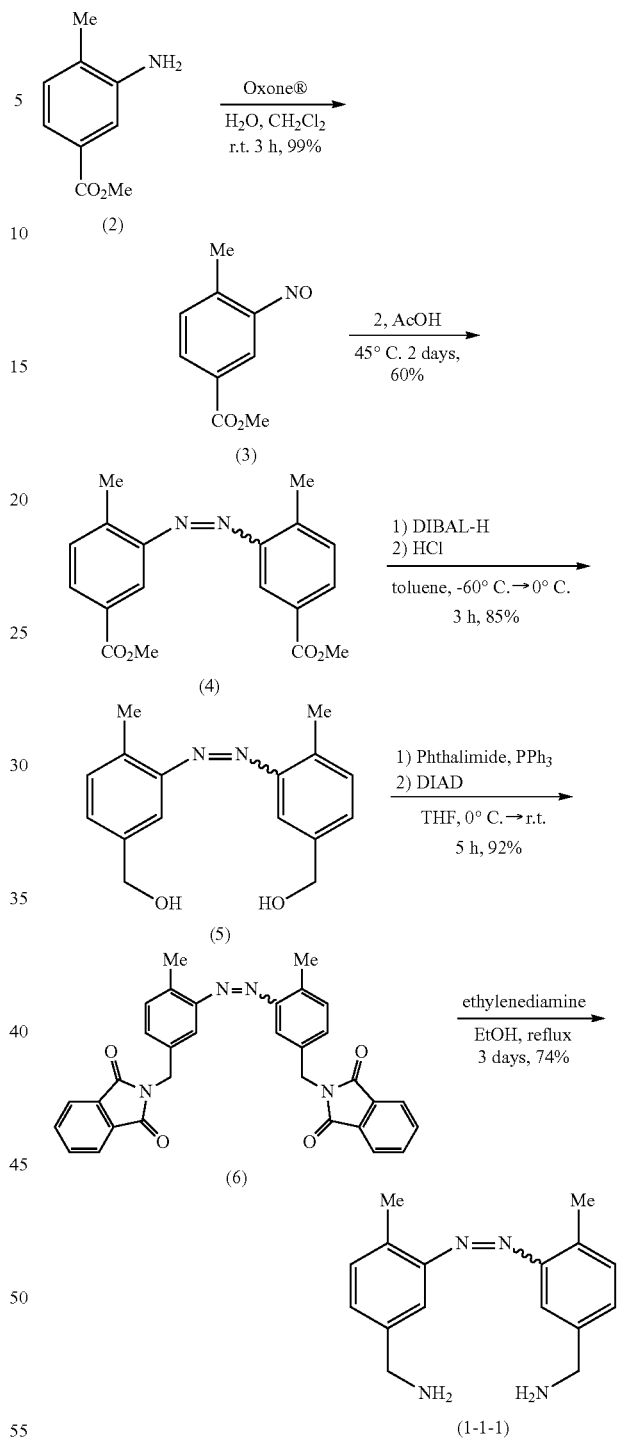

Synthesis of Compound (3)

Commercially available methyl 3-amino-4 methylbenzoate (hereinafter, also referred to as "Compound (2)", 500 mg, 3.03 mmol, Ark Pharm, inc.) was weighed in a 300 ml eggplant flask, dichloromethane (8.28 ml) was added thereto, and the mixture was stirred. Oxone (trade name) (3742 mg, 6.06 mmol) was weighed into a 100 ml Erlenmeyer flask, water (37 ml) was added thereto, and the mixture was stirred. This aqueous solution was added to the first solution described and stirred vigorously for 3 hours. Thereafter, the mixture was transferred to a separatory funnel to separate an aqueous layer, and the organic layer was washed with 1N hydrochloric acid, a saturated sodium bicarbonate solution, water, and saturated saline. Then, sodium sulfate was added thereto to dry. Sodium sulfate was removed by filtration, and the solvent was distilled off to obtain Compound (3) (orange, solid, 537.2 mg) at a crude yield of 99%. Compound (3) was not further purified and used as it was for the synthesis of Compound (4).

Synthesis of Compound (4)

Methyl 3-amino-4 methylbenzoate (2,411 mg, 2.49 mmol) and acetic acid (22.0 ml) were added to the synthesized Compound 3, and the mixture was stirred at 45° C. for 2 days. Then, an orange solid was precipitated. This solid was filtered by suction, and washed with water to obtain Compound 4 (orange, solid, 583.4 mg) at a yield of 60% (two-stage yield).

$^1$H-NMR (400 MHz, CDCl$_3$)δ(ppm): 2.81 (s, 6H), 3.94 (s, 6H), 7.43 (d, 2H, J=8.0 Hz), 8.04 (dd, 2H, J=7.9, 1.7 Hz), 8.24 (d, 2H, J=1.7 Hz)

$^{13}$C-NMR (100 MHz, CDCl$_3$)δ(ppm): 18.0, 52.2, 117.2, 128.7, 131.4, 131.5, 143.4, 150.7, 166.9

Synthesis of Compound (5)

Compound (4) (512.4 mg, 1.53 mmol) was weighed in a 100 ml eggplant flask, dried under reduced pressure, and then placed in an argon atmosphere. Dehydrated THF (20 ml) was added thereto and cooled to −78° C., and diisobutylaluminum hydride (1.0 M THF solution, 7.7 ml) was added dropwise thereto. The temperature was raised from −78° C. to 0° C. and stirred at 0° C. for 3 hours. Thereafter, 1 N hydrochloric acid was added thereto to adjust the pH to 3.0. The mixture was allowed to stand until the temperature reached normal temperature, transferred to a separatory funnel, and extracted with tetrahydrofuran (THF). Then, the organic layer was dried over sodium sulfate. Sodium sulfate was removed by filtration, and the solvent was distilled off. The resultant solid was washed with dichloromethane to obtain Compound (5) (orange, solid, 360.8 mg) at a yield of 85%.

$^1$H-NMR (400 MHz, DMSO-d$_6$)δ(ppm): 2.67 (s, 6H), 4.53 (d, 4H, J=5.8 Hz), 5.26 (t, 2H, J=5.8 Hz), 7.39 (s, 4H), 7.54 (s, 2H)

$^{13}$C-NMR (100 MHz, DMSO-d$_6$)δ(ppm): 17.0, 62.4, 113.4, 129.2, 131.1, 135.7, 141.1, 150.2

Synthesis of Compound (6)

Compound (5) (150.0 mg, 0.56 mmol), triphenylphosphine (351.5 mg, 1.34 mmol), and phthalimide (197.2 mg, 1.34 mmol) were weighed into a 100 ml eggplant flask, dried under reduced pressure, and then placed in an argon atmosphere. Dehydrated THF (8 mL) was added thereto, and the mixture was cooled to 0° C. Diisopropyl azodicarboxylate (0.705 ml, 1.34 mmol) was added dropwise thereto, and the temperature was raised from 0° C. to normal temperature. Then, the mixture was stirred for 5 hours. After stirring, the precipitated solid was collected by filtration and washed with THF to obtain Compound (6) (orange, solid, 273.3 mg) at a yield of 92%.

$^1$H-NMR (400 MHz, CDCl$_3$)δ(ppm): 2.66 (s, 6H), 4.86 (s, 4H), 7.27 (d, 2H), J=8.49 Hz, 7.41 (dd, 2H, J=7.82, 1.79 Hz), 7.62 (d, 2H, J=1.65 Hz), 7.40 (dd, 2H, J=5.45, 3.03 Hz), 7.84 (dd, 4H, J=5.41, 3.08 Hz)

$^{13}$C-NMR (100 MHz, CDCl$_3$)δ(ppm): 17.5, 41.4, 116.1, 123.5, 130.8, 131.8, 132.3, 134.1, 134.8, 137.9, 151.1, 168.2

Synthesis of Compound (1-1-1)

Compound (6) (288.8 mg, 0.55 mmol) was weighed into a 30 ml two-diameter eggplant flask and dried under reduced pressure. Then, ethanol (2.9 ml) was added thereto under an argon atmosphere. Ethylenediamine (146 μl, 2.19 mmol) was added dropwise thereto at room temperature, and then, the mixture was stirred for 3 days under reflux. After left to cool to room temperature, the mixture was transferred to a separatory funnel, water was added thereto, and the mixture was extracted with dichloromethane. Next, 1 N hydrochloric acid was added to the organic layer, and an extraction operation was performed with the separatory funnel. An aqueous sodium hydroxide solution was added to the obtained aqueous layer to make the aqueous layer basic (pH=12). Then, the aqueous layer was transferred to a separatory funnel, extracted with dichloromethane, and dried over sodium sulfate. Sodium sulfate was removed by filtration, the solvent was distilled off, and the residue was subjected to column chromatography (methanol:aqueous ammonia=25:1) to obtain Compound (1-1-1) (orange, solid, 107.7 mg) at 74%.

trans-Azobenzene Form (1-1-1)

$^1$H-NMR (400 MHz, CD$_3$OD)δ(ppm): 2.71 (s, 6H), 3.82 (s, 4H), 7.35 (d, 2H, J=7.84 Hz), 7.39 (dd, 2H, J=7.77, 1.62 Hz), 7.59 (s, 2H)

$^{13}$C-NMR (100 MHz, CD$_3$OD)δ(ppm): 17.5, 46.3, 115.7, 131.1, 132.6, 137.8, 142.0, 152.4 cis-Azobenzene form (1-1-1)

$^1$H-NMR (400 MHz, CD$_3$OD)δ(ppm): 2.31 (s, 6H), 3.48 (s, 4H), 6.21 (s, 2H), 7.07 (d, 2H, J=7.75), 7.19 (d, 2H, J=7.78)

$^{13}$C-NMR (100 MHz, CD$_3$OD)δ(ppm): 17.1, 45.9, 116.8, 127.9, 130.7, 132.1, 141.8, 154.4

[Evaluation of CO$_2$ Adsorption]

Compound (1-1-1), which is a trans-azobenzene form, (hereinafter, also referred to as "trans (1-1-1)". 50.0 mg) was weighed into a 50 ml eggplant flask, and a septum was attached. Then, chloroform (6.0 ml) was added thereto using a syringe, and Compound (1-1-1) was completely dissolved using ultrasonic waves. When CO$_2$ was bubbled into the solution from a CO$_2$ (99.9%, 0.45 L) balloon attached with a syringe needle, an orange solid was precipitated. The solid was collected by suction filtration, dried under reduced pressure at room temperature for 2 days, and then the dried solid was analyzed by elemental analysis. The results are shown in Table 1.

TABLE 1

|  | C | H | N | O |
|---|---|---|---|---|
| Atomic weight | 12.011 | 1.008 | 14.007 | 15.999 |
| Measured wt % | 65.74 | 6.433 | 17.65 | 10.18 |
| Predicted wt % for trans-(1-1-1) | 71.61 | 7.51 | 20.88 | 0 |
| Predicted wt % for trans-(1-1-1)•CO$_2$ | 65.37 | 6.45 | 17.94 | 10.24 |
| Predicted wt % for trans-(1-1-1)•(CO$_2$)$_2$ | 60.66 | 5.66 | 15.72 | 17.96 |

It can be seen from Table 1 that, when the measured values are in agreement with the predicted values, the resultant solid corresponds to a molecule provided by bonding of trans (1-1-1) and $CO_2$ at a ratio of 1:1.

[Evaluation of $CO_2$ Release]

The $CO_2$ adduct of trans (1-1-1) (precipitated solid) was added in a certain amount (x [mg]) to a NMR tube and dried under reduced pressure. Under an argon atmosphere, deuterated chloroform (0.6 ml) was added thereto, and ultrasonic waves were applied thereto to prepare a suspension. This suspension was irradiated with UV light (365 nm) for 1.5 h using a UV irradiation device (30.4 mW/cm$^2$, 365 nm, lamp house: USHIO Optical ModuleX OPM2-502 HQ, power supply device: BA-H 502, compatible lamp: USH-500 SC2, heat absorbing filter: HAF-50S-30H, ultraviolet transmitting—visible absorbing filter: UTVAF-50S-36U), and then subjected to $^1$H-NMR measurement.

Upon irradiation with UV light, the $CO_2$ adduct of trans (1-1-1) was dissolved in deuterated chloroform. Peaks of trans (1-1-1) and Compound (1-1-1) as a cis-azobenzene form (hereinafter, also referred to as "cis (1-1-1)") were observed in $^1$H-NMR. Since no $CO_2$ adduct of trans (1-1-1) (solid insoluble in deuterated chloroform) and no $CO_2$ adduct of cis (1-1-1) were observed, it is presumed that $CO_2$ was released from the $CO_2$ adduct of trans (1-1-1) and exited the system.

(Calculation of $CO_2$ Adsorption Efficiency by Weight Change)

trans (1-1-1) was metered into a 30 ml vial, and the weight was measured. Chloroform (6 ml) was added thereto, and air ($CO_2$ concentration: about 500 ppm, humidity: about 5%) or $CO_2$ (99.9%, 0.45 L with balloon and needle) was bubbled therethrough. The solvent was distilled off, the weight was measured again after drying under reduced pressure, and the weights before and after introduction of $CO_2$ were compared.

Air Bubbling

When 11.32 mg of trans (1-1-1) was used, the weight increased by 0.58 mg after air bubbling. The increase was taken as $CO_2$ absorbed, and the absorption efficiency was determined from the following calculation formula.

$$\text{Absorption efficiency (\%)} = \{(\text{weight increase}/\text{molecular weight of } CO_2))/(\text{weight of trans}(1\text{-}1\text{-}1)/\text{molecular weight of trans}(1\text{-}1\text{-}1))\} \times 100 = \{(0.58/44.01)/(11.32/268.36)\} \times 100 = 31.2\% \text{ (i.e. approximately 30\%)}$$

$CO_2$ Bubbling

When 11.02 mg of trans (1-1-1) was used, the weight increased by 1.88 mg after $CO_2$ bubbling. The increase was taken as $CO_2$ absorbed, and the absorption efficiency was determined from the following calculation formula.

$$\text{Absorption efficiency (\%)} = \{(\text{weight increase}/\text{molecular weight of } CO_2))/(\text{weight of trans}(1\text{-}1\text{-}1)/\text{molecular weight of trans}(1\text{-}1\text{-}1))\} \times 100 = \{(1.88/44.01)/(11.02/268.36)\} \times 100 \; 104\% \text{ (i.e. approximately 100\%)}$$

(Calculation of $CO_2$ Release Efficiency Using NDIR (Non-Dispersive Infrared Absorption Method))

A schematic view of an apparatus for use in a non-dispersive infrared absorption method is shown in FIG. 1. As shown in FIG. 1, a NDIR carbon dioxide concentration meter (GC-02, coxfox) was placed in a desiccator (RVD-250, AS ONE, 6.5 L) having valves each attached to the upper part and to the side, and the valve on the upper part and a bubbler were connected with a rubber hose (inner diameter 6 mm, 30 cm).

A $CO_2$ adduct of trans (1-1-1) (22 mg) was metered into a stoppered test tube (inner diameter: 15 mm, total height: 13 cm), and the test tube was attached and sealed with a three-way cock having a ground glass joint.

The valve on the side of the desiccator and the three-way cock were connected with a rubber hose (25 cm), and chloroform (1 ml) was added to the test tube using a syringe. UV light (365 nm) was applied using the same UV irradiation device as described above under stirring with a stirrer. The value of the carbon dioxide concentration meter was recorded every 10 minutes. The measurement results are as shown in FIG. 2.

Figure 2:
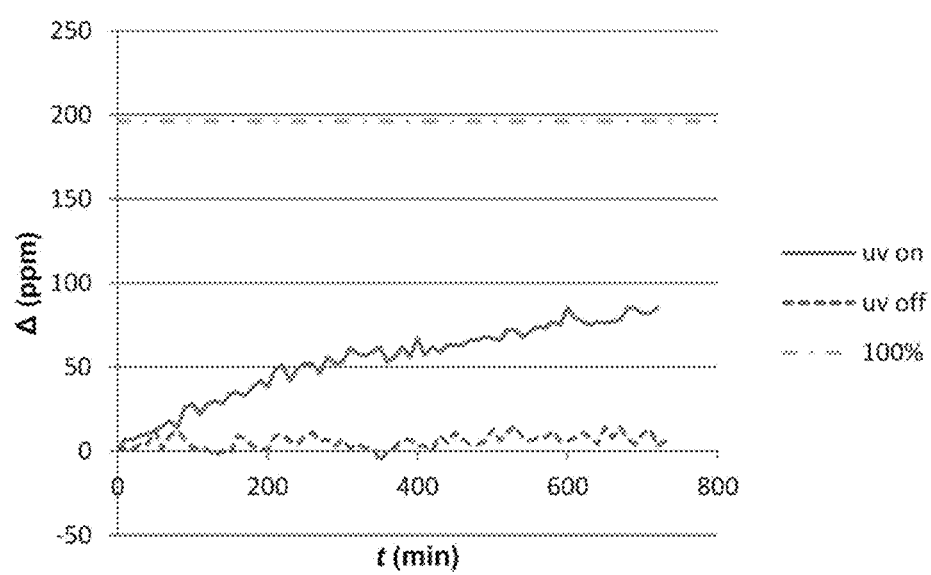
FIG. 2 shows measurement results of a carbon dioxide concentration meter by a non-dispersive infrared absorption method (NDIR).

It can be seen from FIG. 2 that the $CO_2$ adduct of trans (1-1-1) releases $CO_2$ by being irradiated with UV light. From the measurement results of FIG. 2, it is found that the amount of $CO_2$ released is 80.2 ppm.

"100%" in FIG. 2 indicates the predicted value of a measurement result in a case in which 100% of $CO_2$ absorbed by the $CO_2$ absorbent is released. In addition, "uv off" in FIG. 2 represents the reference line at which no carbon dioxide is released by ultraviolet light irradiation, and shows the transition (measurement result) of the carbon dioxide concentration under the condition of no ultraviolet light irradiation and no $CO_2$ adduct of trans (1-1-1) (condition of only chloroform).

Here, the $CO_2$ release efficiency is calculated as follows. When the value of the carbon dioxide concentration meter increased by y [ppm] in use of x [mg] of the $CO_2$ adduct of trans (1-1-1), the amount of $CO_2$ released was estimated by the following calculation formula, and the $CO_2$ release efficiency was calculated.

$CO_2$ release efficiency (%)=(amount of released $CO_2$)/(amount of substance of $CO_2$ adduct of trans (1-1-1))×100={(y×10$^{-6}$× capacity of desiccator (L))/22.4)}/{x/1000/(molecular weight of $CO_2$ adduct of trans (1-1-1))}×100={(y×10$^{-6}$×6.5)/22.4)}/(x/1000/312.37)×100

From the above results, when 22.0 mg of the $CO_2$ adduct of trans (1-1-1) was used, an increase of 80.2 ppm in the $CO_2$ concentration was observed. Thus, the $CO_2$ release efficiency was determined from the formula described above as follows.

$$CO_2 \text{ release efficiency (\%)} = [\{(80.2 \times 10^{-6} \times 6.5)/22.4\}/\{17.8/1000/312.37\}] \times 100 = 40.8\% \text{ (i.e. approximately 41\%)}$$

The measurement results for Compound (1-1-1) obtained in Example 1 are shown in Table 2.

(Calculation of $CO_2$ Release Efficiency in a Case in which Carbon Dioxide Absorption/Release Agent was Repeatedly Used)

Figure 3:
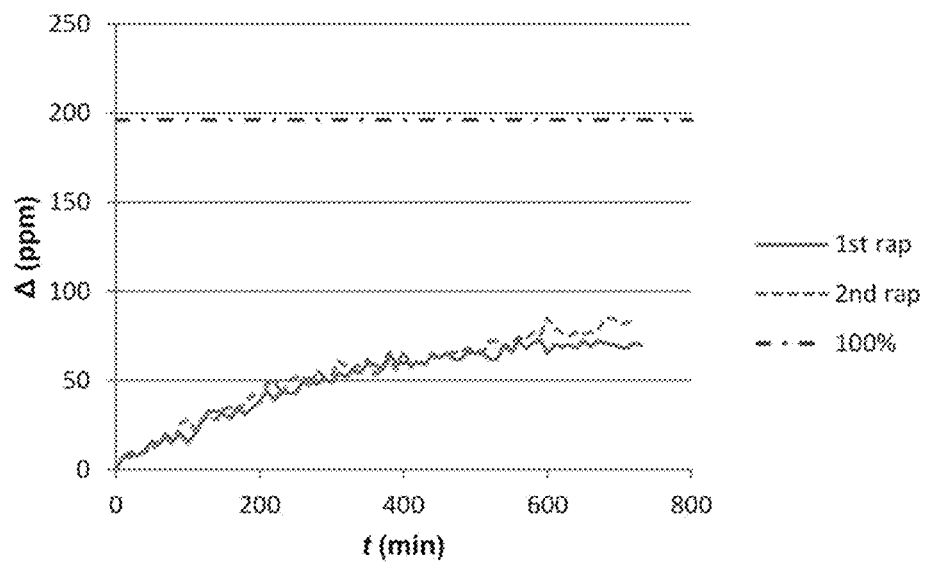
FIG. 3 shows measurement results of a carbon dioxide concentration meter by a non-dispersive infrared absorption method when the carbon dioxide absorption/release agent of the present embodiment is repeatedly used.

The calculation of the $CO_2$ release efficiency in a case where the carbon dioxide absorption/release agent was repeatedly used was measured by the following steps. A case in which the operations in the following step A) to step B) were performed was taken as a first round, and thereafter, a case in which the operations in step C) to step D) were performed was taken as a second round. The results are shown in FIG. 3.

Step A): A test tube containing trans (1-1-1) as a $CO_2$ absorbent and chloroform was attached to the same measuring apparatus as in FIG. 1. Thereafter, the $CO_2$ concentration was recorded every 10 minutes under irradiation with UV light (365 nm).

Step B): After the measurement was completed, the test tube was removed from the apparatus, chloroform was distilled off, and then methanol was added to completely dissolve the solid.

Step C): Methanol was distilled off, then chloroform was added, and bubbling with $CO_2$ was conducted.

Step D): After chloroform was distilled off, the test tube was attached to the same measuring apparatus as in FIG. 1, and chloroform was metered and added with a syringe. The $CO_2$ concentration was measured every 10 minutes under irradiation with UV light.

As can be seen from FIG. 3, the $CO_2$ adduct of trans (1-1-1) releases $CO_2$ by being irradiated with UV light. From the measurement results in FIG. 3, the amount of $CO_2$ released in the first round is 70.2 ppm, and the amount of $CO_2$ released in the second round is 80.2 ppm, both of which are comparable. It can thus be seen that repeated use of the carbon dioxide absorption/release agent of the present embodiment would not lead to decrease in the $CO_2$ release efficiency.

"100%" in FIG. 3 indicates a predicted value of a measurement result in a case in which 100% of $CO_2$ absorbed by the $CO_2$ absorbent is released.

Example 2

The same operations as in Example 1 were conducted except that Compound (1-3) was prepared in accordance with the synthesis route shown below. The following synthesis route indicates a synthesis route for finally obtaining Compound (1-3) using Compound (7) as a starting material. The results are shown in Table 2.

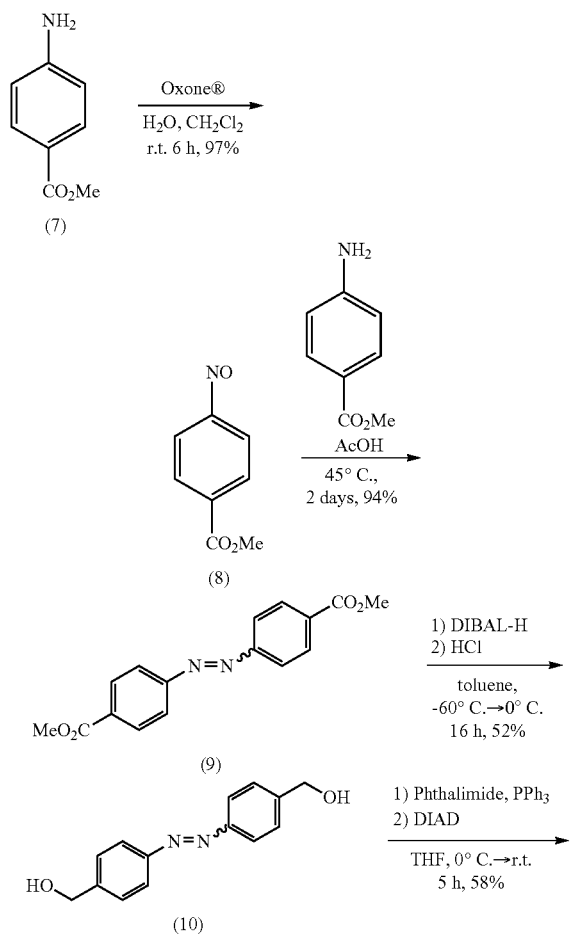

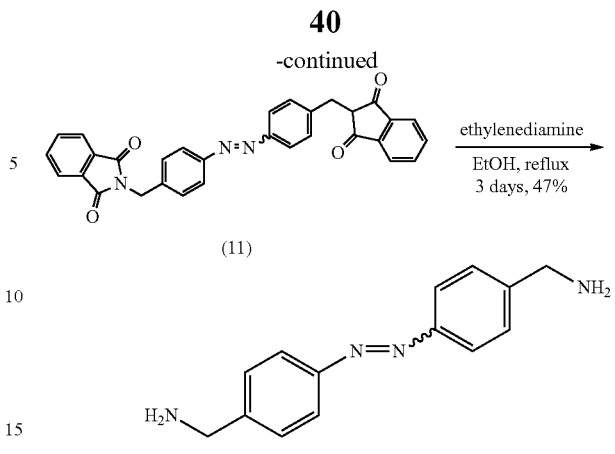

Synthesis of Compound (8)

Commercially available methyl 4-aminobenzoate (hereinafter, also referred to as "Compound (7)", 500 mg, 3.31 mmol, TCI) was weighed into a 300 ml eggplant flask, dichloromethane (9.1 ml) was added thereto, and the mixture was stirred. Oxone (R) (4067 mg, 6.62 mmol) was weighed into a 100 mL Erlenmeyer flask, water (41 ml) was added thereto, and the mixture was stirred. This aqueous solution was added to the initial solution and stirred vigorously for 6 hours. Thereafter, the mixture was transferred to a separatory funnel to separate an aqueous layer, and the organic layer was washed with 1 N hydrochloric acid, a saturated aqueous sodium bicarbonate solution, water, and saturated saline. Then, sodium sulfate was added thereto, and the organic layer was dried. Sodium sulfate was removed by filtration, and the solvent was distilled off to obtain Compound (8) (orange, solid, 533.8 mg) at a crude yield of 98%. Compound (8) was not further purified and used as it was for the synthesis of Compound (9).

Synthesis of Compound (9)

Methyl 4-aminobenzoate (Compound (7), 407.2 mg, 2.69 mmol) and acetic acid (23.8 ml) were added to the synthesized Compound (8), and the mixture was stirred at 45° C. for 2 days. Then, an orange solid was precipitated. This solid was filtered by suction, and washed with water to obtain Compound (9) (orange, solid, 797.5 mg) at a yield of 91% (two-stage yield).

Synthesis of Compound (10)

Compound (9) (797.5 mg, 2.95 mmol) was weighed into a 100 ml eggplant flask, vacuum-dried, and then placed in an argon atmosphere. Dehydrated THF (29.5 ml) was added thereto, and the mixture was cooled to −78° C. Then, diisobutylaluminum hydride (1.0M THF solution, 14.8 ml) was added dropwise thereto. The temperature was raised from −78° C. to 0° C., and the mixture was stirred at 0° C. for 3 hours. Thereafter, 1 N hydrochloric acid was added to adjust the pH to 3.0. The mixture was left to stand until normal temperature was reached. After extraction with THF, the organic layer was dried over sodium sulfate. Sodium sulfate was removed by filtration, and the solvent was distilled off. The resultant solid was washed with dichloromethane to obtain Compound (10) (orange, solid, 438.2 mg) at a yield of 61%.

Synthesis of Compound (11)

Compound (10) (438.2 mg, 1.81 mmol), triphenylphosphine (1138.3 mg, 4.34 mmol), and phthalimide (638.5 mg, 4.34 mmol) were weighed into a 100 ml eggplant flask, dried under reduced pressure, and then placed in an argon atmosphere. Dehydrated THF (26.2 ml) was added, and the mixture was cooled to 0° C. Diisopropyl azodicarboxylate (2.28 ml, 4.34 mmol) was added dropwise thereto, and the temperature was raised from 0° C. to normal temperature. Then the mixture was stirred for 2 days. After stirring, the precipitated solid was collected by filtration and washed with THF to obtain Compound (11) (orange, solid, 871.5 mg) at a yield of 96%.

Synthesis of Compound (1-3)

Compound (11) (259.4 mg, 0.52 mmol) was weighed into a 30 ml two-necked eggplant flask and dried under reduced pressure. Then, ethanol (2.8 ml) was added thereto under an argon atmosphere. Ethylenediamine (139 μl, 2.08 mmol) was added dropwise thereto at room temperature, and then, the mixture was stirred for 3 days under reflux. After left to cool to room temperature, the mixture was transferred to a separatory funnel, water was added thereto, and the mixture was extracted with dichloromethane. Next, 1 N hydrochloric acid was added to the organic layer, and an extraction operation was performed with the separatory funnel. An aqueous sodium hydroxide solution was added to the obtained aqueous layer to make the aqueous layer basic (pH=12). Then, the aqueous layer was transferred to a separatory funnel, extracted with dichloromethane, and dried over sodium sulfate. Sodium sulfate was removed by filtration, the solvent was distilled off, and then, the obtained residue was washed with hexane to obtain Compound (1-3) (orange, solid, 58.3 mg) at 47%.

trans-Azobenzene Form (1-3)

$^1$H-NMR (400 MHz, CDCl$_3$)δ(ppm): 3.96 (s, 4H), 7.46 (d, 4H, J=8.32 Hz), 7.89 (d, 4H, J=8.36 Hz)

Comparative Example 1

The same operations as in Example 1 were conducted except that Compound (14) was prepared in accordance with the synthesis route shown below. The results are shown in Table 2.

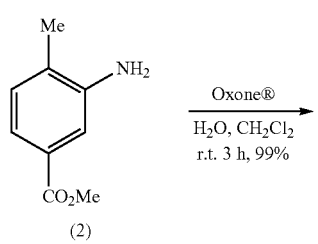

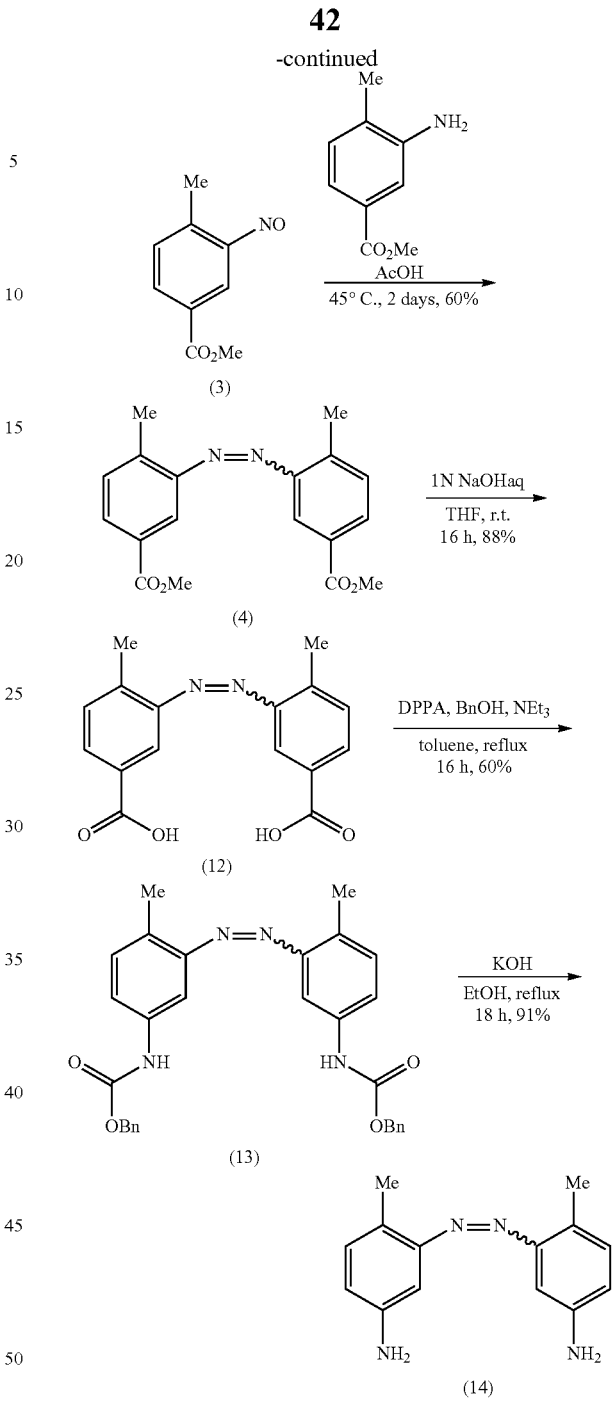

Synthesis of Compound (12)

Compound (4) was synthesized using Compound (2) as a starting material in the same manner as described above.

Then, Compound (4) (2.814 g, 8.62 mmol) was weighed into a 100 ml eggplant flask, and THF (27 ml) was added thereto. After 1 N NaOH (173 mL) was added dropwise with stirring, the mixture was stirred for 16 hours under reflux. The mixture was left to cool to normal temperature, and acidified with 1 N hydrochloric acid until pH=2 or less was reached. The precipitated solid was collected by filtration and washed with water to obtain Compound (12) (Red, solid, 2.26 g) at a yield of 88%.

$^1$H-NMR (400 MHz, DMSO-d$_6$)δ(ppm): 2.76 (s, 6H), 7.59 (d, 2H, J=7.93 Hz), 8.01 (d, 2H, J=7.92 Hz), 8.11 (s, 2H)

Synthesis of Compound (13)

Compound (12) (364.9 mg, 1.32 mmol) was weighed into a 100 ml two-diameter eggplant flask and dried under reduced pressure. Then, toluene (15.2 ml) was added thereto under an argon atmosphere. Benzyl alcohol (0.285 ml, 2.74 mmol), triethylamine (0.38 ml, 2.73 mmol), and diphenylphosphoryl azide (0.59 ml, 2.73 mmol) were added thereto at room temperature, and then the mixture was were stirred for 16 hours under reflux. The precipitated solid was collected by filtration and washed with dichloromethane and methanol to obtain Compound (13) (orange, solid, 402.0 mg) at a yield of 60%.

$^1$H-NMR (400 MHz, CDCl$_3$)δ(ppm): 2.68 (s, 6H), 5.21 (s, 4H), 6.68 (brs, 2H), 7.25-7.43 (m, 12H), 7.51-7.59 (m, 4H)

Synthesis of Compound (14)

Compound (13) (402.0 mg, 0.79 mmol) was weighed into a 300 ml eggplant flask, and a saturated potassium hydroxide ethanol solution (67.8 ml) was added thereto. The mixture was stirred for 18 hours under reflux. The mixture was left to cool to room temperature and neutralized with an aqueous NH$_4$Cl solution. After ethanol was distilled off, the solution was transferred to a separatory funnel and extracted with dichloromethane. The resultant organic layer was washed with water and dried over sodium sulfate. Sodium sulfate was removed by filtration, and the solvent was distilled off. The residue was subjected to column chromatography (hexane:ethyl acetate=4:1) to obtain Compound (14) (Red, solid, 173.4 mg) at a yield of 91%.

$^1$H-NMR (400 MHz, CDCl$_3$)δ(ppm): 2.62 (s, 6H), 3.65 (brs, 4H), 6.74 (dd, 2H, J=8.08, 2.50 Hz), 6.98 (d, 2H, J=2.47 Hz), 7.12 (d, 2H, J=8.09 z), 7.26 (s, 2H)

TABLE 2

| Compound | Absorption efficiency (%) | | Release efficiency (%) |
|---|---|---|---|
| | Air bubbling | CO$_2$ bubbling | |
| Example 1 Compound (1-1-1) | 30 | 100 | 41 |
| Example 2 Compound (1-3) | — | 100 | 9.6 |
| Comparative Example 1 Compound (14) | 0 | 0 | — |

From Table 2, it was found that the compounds obtained in Examples have an adsorption capacity and a release capacity of carbon dioxide. Here, the compounds obtained in Comparative Examples were inferior in the adsorption capacity and release capacity of carbon dioxide to those of Examples.

Example 3

The same operations as in Example 1 were conducted except that Compound (1-2) was prepared in accordance with the synthesis route shown below. The following synthesis route indicates a synthesis route for finally obtaining Compound (1-2) using Compound (12) as a starting material. The results are shown in Table 3.

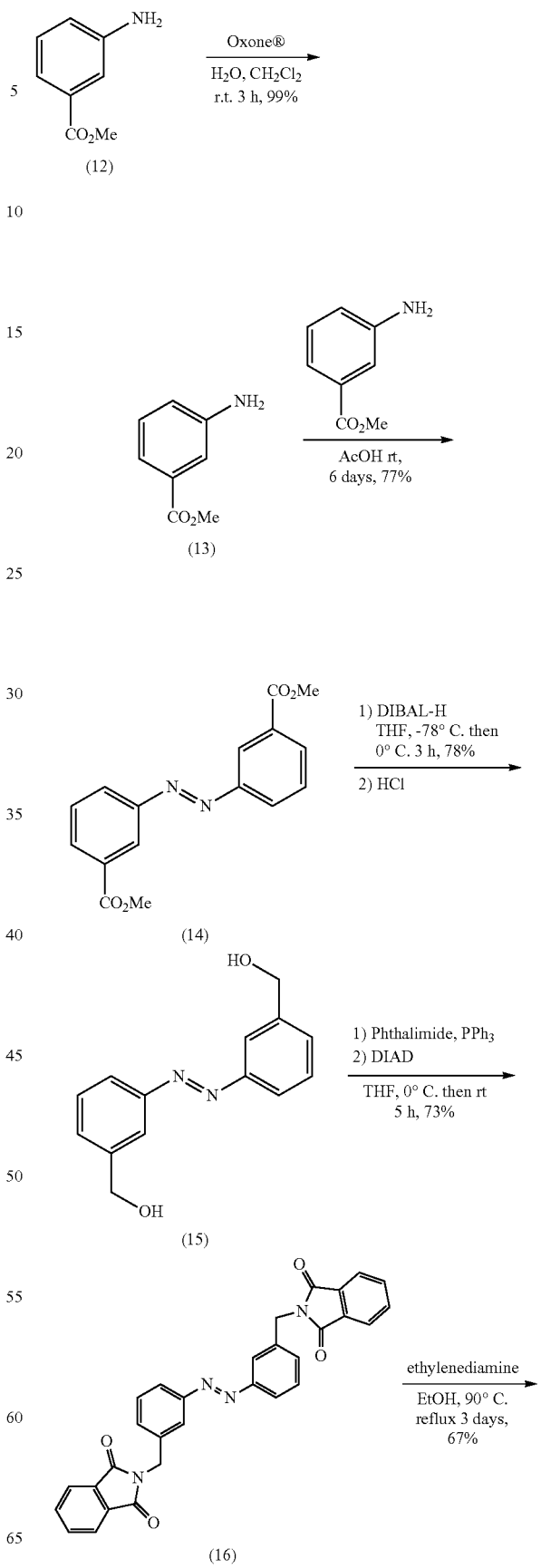

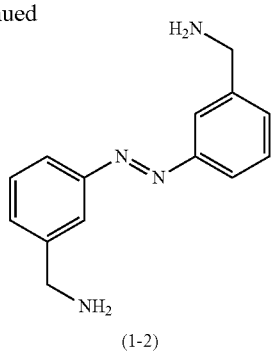

(1-2)

Synthesis of Compound (13)

Commercially available methyl 3-aminobenzoate (hereinafter, also referred to as "Compound (12)", 500 mg, 1.65 mmol, TCI) was weighed into a 100 ml eggplant flask, dichloromethane (4.5 mL) was added thereto, and the mixture was stirred. Oxone (R) (2028 mg, 3.30 mmol) was weighed into a 100 ml Erlenmeyer flask, water (20 ml) was added thereto, and the mixture was stirred. This aqueous solution was added to the initial solution and stirred vigorously for 3 hours. Thereafter, the mixture was transferred to a separatory funnel to separate an aqueous layer, and the organic layer was washed with 1 N hydrochloric acid, a saturated aqueous sodium bicarbonate solution, water, and saturated saline. Then, sodium sulfate was added thereto, and the organic layer was dried. Sodium sulfate was removed by filtration, and the solvent was distilled off to obtain Compound (13) (orange, solid, 272.4 mg) at a crude yield of 99%. Compound (13) was not further purified, and was used as it was for the synthesis of Compound (14).

Synthesis of Compound (14)

Methyl 3-aminobenzoate (Compound (12), 205.5 mg, 1.36 mmol) and acetic acid (12.0 ml) were added to the synthesized Compound (13), and the mixture was stirred at room temperature for 6 days. Then, an orange solid was precipitated. This solid was filtered by suction, and washed with water to obtain Compound (14) (orange, solid, 313.3 mg) at a yield of 77% (two-stage yield).

Synthesis of Compound (15)

Compound (14) (313.3 mg, 1.05 mmol) was weighed into a 100 ml eggplant flask, vacuum-dried, and then placed in an argon atmosphere. Dehydrated THF (10.5 ml) was added thereto, and the mixture was cooled to −78° C. Then, diisobutylaluminum hydride (1.0 M THF solution, 4.2 ml) was added dropwise thereto. The temperature was raised from −78° C. to 0° C., and the mixture was stirred at 0° C. for 3 hours. Thereafter, 1 N hydrochloric acid was added to adjust the pH to 3.0. The mixture was left to stand until normal temperature was reached and transferred to a separatory funnel. After extraction with THF, the organic layer was dried over sodium sulfate. Sodium sulfate was removed by filtration, and the solvent was distilled off to obtain Compound (15) (orange, solid, 189.0 mg) at a yield of 78%.

Synthesis of Compound (16)

Compound (15) (189.0 mg, 0.78 mmol), triphenylphosphine (490.5 mg, 1.87 mmol), and phthalimide (275.1 mg, 1.87 mmol) were weighed into a 100 ml eggplant flask, dried under reduced pressure, and then placed in an argon atmosphere. Dehydrated THF (11.3 ml) was added thereto, and the mixture was cooled to 0° C. Diisopropyl azodicarboxylate (0.98 ml, 1.87 mmol) was added dropwise thereto, and the temperature was raised from 0° C. to normal temperature. Then the mixture was stirred for 5 hours. After stirring, the precipitated solid was collected by filtration and washed with THF to obtain Compound (16) (orange, solid, 283.7 mg) at a yield of 73%.

Synthesis of Compound (1-2)

Compound (16) (283.7 mg, 0.57 mmol) was weighed into a 30 ml two-necked eggplant flask and dried under reduced pressure. Then, ethanol (3.0 ml) was added thereto under an argon atmosphere. Ethylenediamine (152 µl, 2.28 mmol) was added dropwise thereto at room temperature, and then, the mixture was stirred for 3 days while being refluxed. After left to cool to room temperature, the mixture was transferred to a separatory funnel, water was added thereto, and the mixture was extracted with dichloromethane. Next, 1 N hydrochloric acid was added to the organic layer, and an extraction operation was performed with the separatory funnel. An aqueous sodium hydroxide solution was added to the obtained aqueous layer to make the aqueous layer basic (pH=12). Then, the aqueous layer was transferred to a separatory funnel, extracted with dichloromethane, and dried over sodium sulfate. Sodium sulfate was removed by filtration, and the solvent was distilled off. Then the obtained residue was subjected to silica gel column chromatography to obtain Compound (1-2) (orange, solid, 92.5 mg) at 67%.

trans-Azobenzene Form (1-2)

$^1$H-NMR (400 MHz, CDCl$_3$)δ(ppm): 3.99 (s, 4H), 7.44 (m, 4H), 7.80 (d, 2H, J=7.64 Hz), 7.87 (s, 2H)

$^{13}$C-NMR (100 MHz, CDCl$_3$)δ(ppm): 45.3, 113.7, 120.9, 128.3, 128.7, 143.5, 151.9

Example 4

The same operations as in Example 1 were conducted except that Compound (2-1-1) was prepared in accordance with the synthesis route shown below. The following synthesis route indicates a synthesis route for finally obtaining Compound (2-1-1) using Compound (5) synthesized in Example 1 as a starting material. The results are shown in Table 3.

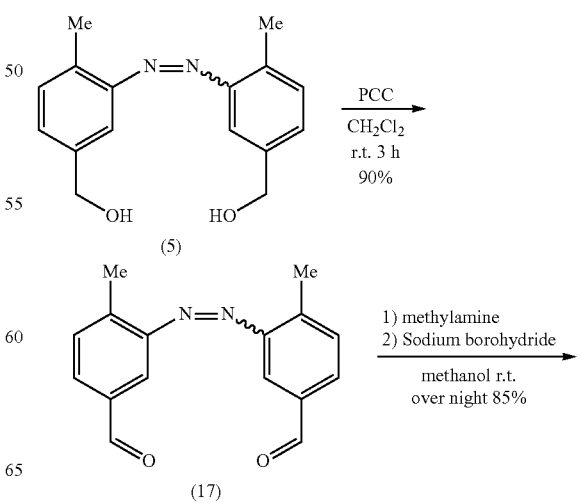

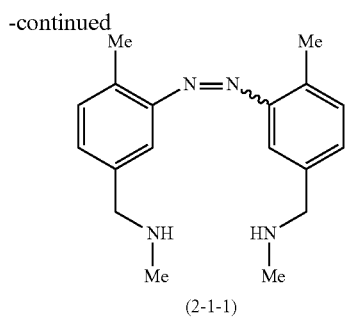

(2-1-1)

Synthesis of Compound (17)

Compound (5) (250.0 mg, 0.925 mmol) and molecular sieves 4A (750 mg) were weighed into a 50 ml two-necked eggplant flask, dried under reduced pressure, and then placed in an argon atmosphere. Dehydrated THF (4.2 mL) was added, pyridinium chlorochrochromate (PCC) (599.2 mg, 2.78 mmol) was added thereto under an argon atmosphere, and then, the mixture was heated under reflux at 90° C. for 4.5 hours. After completion of the reaction, the reaction solution was allowed to cool, filtered through celite, and then, the solvent in the filtrate was distilled off under reduced pressure. The residue was subjected to silica gel column chromatography (hexane:ethyl acetate=2:1) to obtain Compound (17) (orange, solid, 222.0 mg) at a yield of 90%.

Synthesis of Compound (2-1-1)

Compound (17) (198.4 mg, 0.747 mmol) was weighed into a 100 ml two-necked eggplant flask, vacuum-dried, and then placed in an argon atmosphere. Dehydrated methanol (7.7 ml) was added thereto, methyl amine (2.0 M methanol solution, 0.747 ml) was added thereto at room temperature, and then the mixture was stirred for 4 hours. Thereafter, sodium borohydride was added thereto at room temperature under an argon atmosphere, and the mixture was stirred overnight. Water (0.74 ml) was added to stop the reaction, the mixture was transferred to a separatory funnel. After ethyl acetate and saturated saline were added to perform an extraction operation, the organic layer was dried over sodium sulfate. Sodium sulfate was removed by filtration, the solvent was distilled off, and the residue was subjected to silica gel column chromatography (methanol:aqueous ammonia=100:1) to obtain Compound (2-1-1) (orange, solid, 188.6 mg) at a yield of 85%.

trans-Azobenzene Form (2-1-1)

$^1$H-NMR (400 MHz, CDCl$_3$)δ(ppm): 2.47 (s, 6H), 2.71 (s, 6H), 3.77 (s, 4H), 7.29 (d, 2H, J=7.79 Hz), 7.33 (dd, 2H, J=7.79, 1.63 Hz), 7.52 (s, 2H)

Example 5

The same operations as in Example 1 were conducted, except that Compound (2-3-1) was prepared according to the synthesis route shown below and that the carbon dioxide release efficiency in the two-step process of absorption and release was calculated from measurement of the amount of CO$_2$ released using NDIR (non-dispersive infrared absorption method) to thereby evaluate the carbon dioxide absorption/release capacity without conducting the "CO$_2$ release evaluation" in the same manner as in Example 1 (i.e., without calculating the carbon dioxide release efficiency by weight). The following synthesis route indicates a synthesis route for finally obtaining Compound (2-3-1) using Compound (5) synthesized in Example 1 as a starting material. The results are shown in Table 3.

A method of calculating the carbon dioxide release efficiency in the two-step process of absorption and release will be described in detail hereinafter.

(Calculation of Carbon Dioxide Release Efficiency in Two-Step Process of Absorption and Release Using NDIR (Non-Dispersive Infrared Absorption Method))

The solid absorbed carbon dioxide, which had been precipitated in the carbon dioxide absorption experiment of Compound (2-3-1), was not taken out by suction filtration, and subsequently, a carbon dioxide release experiment by UV irradiation was conducted. Then, the carbon dioxide release efficiency in the two-step process of absorption and release was calculated from the measurement result of the amount of CO$_2$ released using NDIR (non-dispersive infrared absorption method). The calculation method is the same as that of the carbon dioxide release efficiency of other Examples. There was a concern that carbon dioxide remained in the solvent (chloroform) regardless of carbon dioxide absorption by Compound (2-3-1) and the amount of carbon dioxide released increased in the carbon dioxide release experiment via UV irradiation. Thus, after the carbon dioxide absorption experiment, the solvent was once distilled off, chloroform was newly added to form a suspension, and a carbon dioxide release experiment via UV irradiation was conducted.

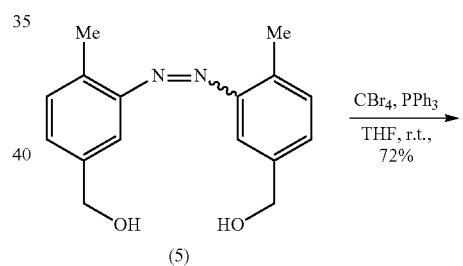

(5)

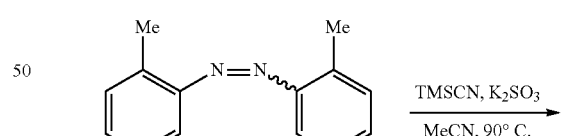

(18)

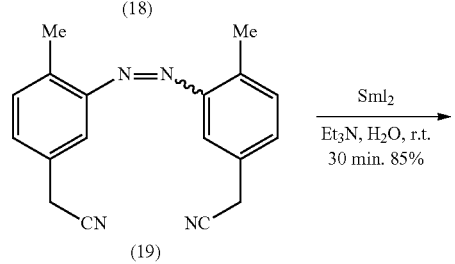

(19)

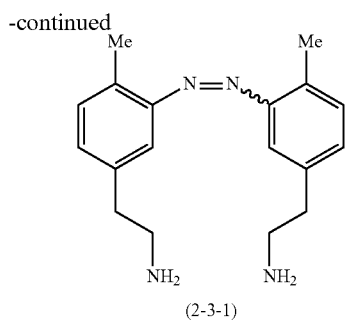

(2-3-1)

Synthesis of Compound (18)—

Triphenylphosphine (484.9 mg, 1.85 mmol) was weighed into a 10 ml pear flask, dried under reduced pressure, and then placed in an argon atmosphere. Dehydrated THF (7.23 ml) was added thereto to give a THF solution of triphenylphosphine. Compound (5) (200.0 mg, 0.740 mmol) and carbon tetrabromide (613.5 mg, 1.85 mmol) were weighed into a 20 ml eggplant flask, dried under reduced pressure, and then placed in an argon atmosphere. Then, dehydrated THF (7.23 ml) was added thereto. The THF solution of triphenylphosphine previously prepared was added to this solution, and the mixture was stirred at room temperature for 24 hours. After stirring, the precipitated solid was collected by filtration and washed with THF. The resultant solid was subjected to silica gel column chromatography (hexane:ethyl acetate=50:1), and the resultant compound was washed with ice-cooled hexane to obtain Compound (18) (orange, solid, 212.5 mg) at a yield of 73%.

Synthesis of Compound (19)

Compound (18) (150.0 mg, 0.378 mmol) and potassium carbonate (125.4 mg, 0.907 mmol) were weighed into a 20 ml two-necked eggplant flask, dried under reduced pressure, and then placed in an argon atmosphere. Dehydrated acetonitrile (1.4 mL) was added thereto, and the mixture was stirred. Trimethylsilyl cyanide (0.14 ml, 1.12 mmol) was added thereto, and the mixture was heated under reflux at 90° C. for 24 hours. Thereafter, the mixture was left to cool to normal temperature, and a 2 N aqueous sodium hydroxide solution was added thereto for dilution. The mixture was transferred to a separatory funnel and extracted with toluene. The organic layer was washed with a 1 N aqueous sodium hydroxide solution and then dried over sodium sulfate. Sodium sulfate was removed by filtration, the solvent was distilled off, and the residue was subjected to silica gel column chromatography (hexane:ethyl acetate=9:1) to obtain Compound (19) (orange, solid, 71.6 mg) at a yield of 66%.

Synthesis of Compound (2-3-1)

Compound (19) (74 mg, 0.256 mmol) was weighed into a 10 ml pear flask, dried under reduced pressure, and then placed in an argon atmosphere. Dehydrated THF (2.0 ml) was added thereto to give a THF solution. A solution of 0.1 M samarium iodide in THF (30.7 ml, 3.07 mmol, Sigma-Aldrich) was added to a 100 ml eggplant flask dried under reduced pressure and then placed in an argon atmosphere. The THF solution of Compound (19) previously prepared was added to this solution at room temperature and stirred. Then, triethylamine (2.02 ml, 18.43 mmol) and water (0.166 ml, 18.43 mmol) were added thereto, and the mixture was stirred vigorously for 20 min. Thereafter, air was bubbled to oxidize an excessive amount of samarium iodide, and dichloromethane and an aqueous sodium hydroxide solution were added thereto to dilute the reaction solution. The mixture was transferred to a separatory funnel and extracted with dichloromethane. The organic layer was washed with an aqueous sodium thiosulfate solution and then dried over sodium sulfate. Sodium sulfate was removed by filtration, the solvent was distilled off, and the residue was subjected to silica gel column chromatography (methanol:aqueous ammonia=10:1) to obtain Compound (2-3-1) (orange, solid, 64.6 mg) at a yield of 85%.

trans-Azobenzene form (2-3-1)

$^1$H-NMR (400 MHz, CD$_3$OD)δ(ppm): 2.69 (s, 6H), 2.78 (t, 4H, J=6.84 Hz), 2.99 (t, 4H, J=6.96 Hz), 7.21 (dd, 2H, J=7.73, 1.75 Hz), 7.27 (d, 2H, J=8.00 Hz), 7.43 (d, 2H, J=1.55 Hz)

$^{13}$C-NMR (100 MHz, CDCl$_3$)δ(ppm): 17.3, 39.8, 43.5, 116.1, 131.2, 131.4, 135.8, 138.1, 151.1

Example 6

The same operations as in Example 1 were conducted except that Compound (2-4-1) was prepared in accordance with the synthesis route shown below. The following synthesis route indicates a synthesis route for finally obtaining Compound (2-4-1) using Compound (20) as a starting material. The results are shown in Table 3.

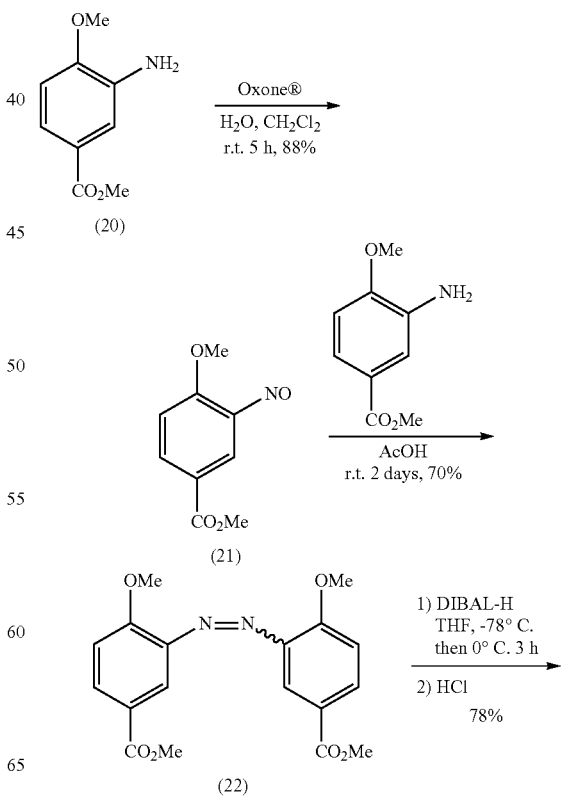

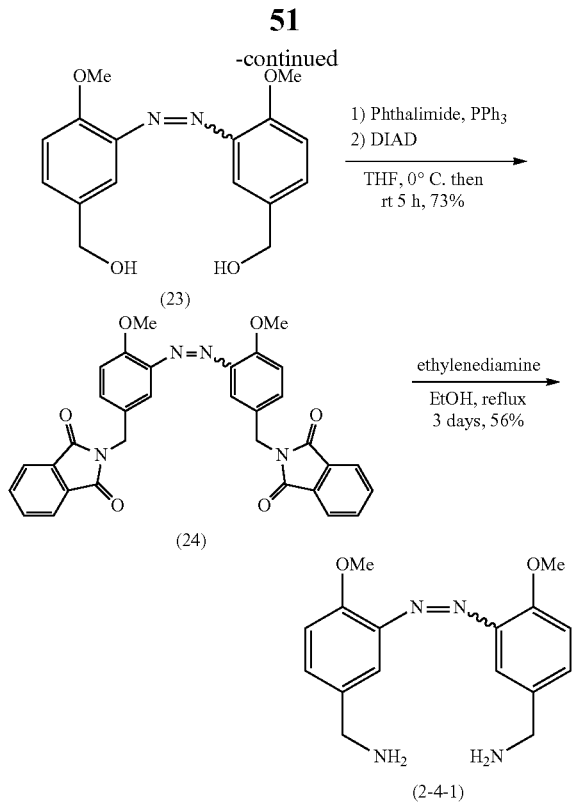

Synthesis of Compound (21)

Commercially available methyl 3-amino-4 methoxybenzoate (hereinafter, also referred to as "Compound (20)", 250 mg, 1.38 mmol, TCI) was weighed into a 100 ml eggplant flask, dichloromethane (3.8 mL) was added thereto, and the mixture was stirred. Oxone (R) (1700 mg, 2.76 mmol) was weighed into a 100 ml Erlenmeyer flask, water (16.7 ml) was added thereto, and the mixture was stirred. This aqueous solution was added to the initial solution, and the mixture was stirred vigorously at room temperature for 5 h. Thereafter, the mixture was transferred to a separatory funnel to separate an aqueous layer, and the organic layer was washed with 1 N hydrochloric acid, a saturated aqueous sodium bicarbonate solution, water, and saturated saline. Then, sodium sulfate was added thereto, and the organic layer was dried. Sodium sulfate was removed by filtration, and the solvent was distilled off to obtain Compound (21) (orange, solid, 218.4 mg) at a crude yield of 88%. Compound (21) was not further purified, and was directly used for synthesis of Compound (22).

Synthesis of Compound (22)

Methyl 3-amino-4 methoxybenzoate (Compound (20), 170.3 mg, 0.93 mmol) and acetic acid (8.2 ml) were added to the synthesized Compound (21), and the mixture was stirred at room temperature for 2 days. Then, an orange solid was precipitated. This solid was filtered by suction, and washed with water to obtain Compound (22) (orange, solid, 280.6 mg) at a yield of 70% (two-stage yield).

Synthesis of Compound (23)

Compound (22) (280.6 mg, 0.78 mmol) was weighed into a 100 ml eggplant flask, dried under reduced pressure, and then placed in an argon atmosphere. Dehydrated THF (7.8 ml) was added thereto, and the mixture was cooled to −78° C. Then, diisobutylaluminum hydride (1.0 M THF solution, 3.9 ml) was added dropwise thereto. The temperature was raised from −78° C. to 0° C., and the mixture was stirred at 0° C. for 18 hours. Thereafter, 1 N hydrochloric acid was added to adjust the pH to 3.0. The mixture was left to stand until normal temperature was reached and transferred to a separatory funnel. After extraction with THF, the organic layer was dried over sodium sulfate. Sodium sulfate was removed by filtration, the solvent was distilled off, and the solid thus obtained was washed with dichloromethane to obtain Compound (23) (orange, solid, 194.6 mg) at a yield of 82%.

Synthesis of Compound (24)

Compound (23) (194.6 mg, 0.64 mmol), triphenylphosphine (405.5 mg, 1.55 mmol), and phthalimide (227.5 mg, 1.55 mmol) were weighed into a 100 ml eggplant flask, dried under reduced pressure, and then placed in an argon atmosphere. Dehydrated THF (9.3 ml) was added, and the mixture was cooled to 0° C. Diisopropyl azodicarboxylate (0.766 ml, 1.55 mmol) was added dropwise thereto, and the temperature was raised from 0° C. to normal temperature. Then the mixture was stirred for 5 hours. After stirring, the precipitated solid was collected by filtration and washed with THF to obtain Compound (24) (orange, solid, 263.9 mg) at a yield of 73%.

Synthesis of Compound (2-4-1)

Compound (24) (595.4 mg, 1.06 mmol) was weighed into a 30 ml two-necked eggplant flask and dried under reduced pressure. Then, ethanol (5.6 ml) was added thereto under an argon atmosphere. Ethylenediamine (283 µl, 4.2 mmol) was added dropwise thereto at room temperature. Then, the temperature was raised, and the mixture was stirred for 3 days under reflux. After left to cool to room temperature, the mixture was transferred to a separatory funnel, water was added thereto, and the mixture was extracted with dichloromethane. Next, 1 N hydrochloric acid was added to the organic layer, and an extraction operation was performed with the separatory funnel. An aqueous sodium hydroxide solution was added to the obtained aqueous layer to make the aqueous layer basic (pH=12). Then, the aqueous layer was transferred to a separatory funnel, extracted with dichloromethane, and dried over sodium sulfate. Sodium sulfate was removed by filtration, and the solvent was distilled off. Then the obtained residue was subjected to silica gel column chromatography (methanol: aqueous ammonia=25:1), and Compound (2-4-1) (orange, solid, 170.6 mg) was obtained at 56%.

trans-Azobenzene Form (2-4-1)

$^1$H-NMR (400 MHz, CDCl$_3$)δ(ppm): 3.85 (s, 4H), 4.02 (s, 6H), 7.05 (d, 2H, J=8.48 Hz), 7.40 (dd, 2H, J=8.48, 2.28 Hz), 7.57 (d, 2H, J=2.24 Hz)

Example 7

The same operations as in Example 1 were conducted except that Compound (2-5-6) was prepared in accordance with the synthesis route shown below. The following synthesis route indicates a synthesis route for finally obtaining Compound (2-5-6) using Compound (7) as a starting material. The results are shown in Table 3.

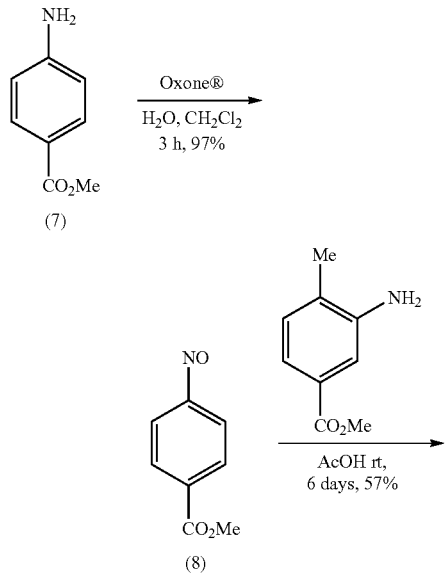

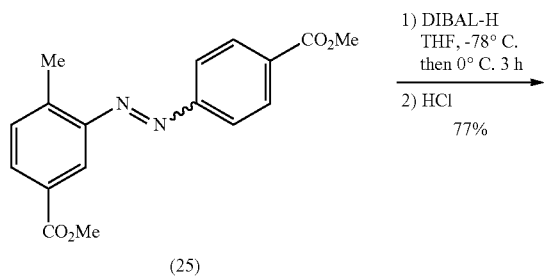

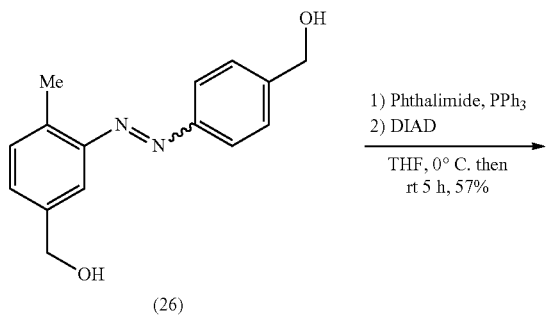

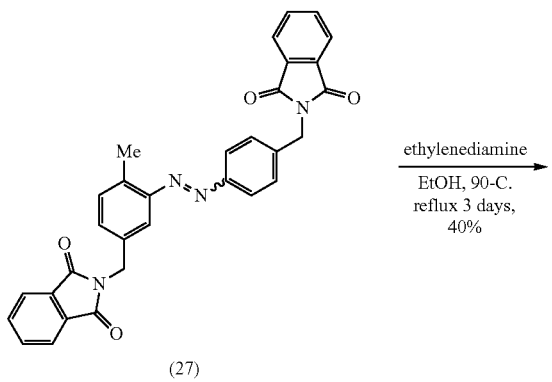

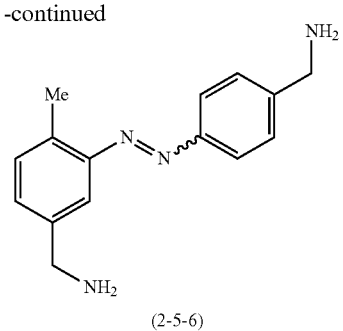

Synthesis of Compound (8)

Compound (8) was synthesized from Compound (7) in the same manner as in Example 2. Compound (7) (250 mg, 1.65 mmol, TCI) was weighed into a 100 ml eggplant flask, dichloromethane (5.0 ml) was added thereto, and the mixture was stirred. Oxone (R) (2028 mg, 3.30 mmol) was weighed into a 100 ml Erlenmeyer flask, water (19.9 ml) was added thereto, and the mixture was stirred. This aqueous solution was added to the initial solution and stirred vigorously for 3 hours. Thereafter, the mixture was transferred to a separatory funnel to separate an aqueous layer, and the organic layer was washed with 1 N hydrochloric acid, a saturated aqueous sodium bicarbonate solution, water, and saturated saline. Then, sodium sulfate was added thereto, and the organic layer was dried. Sodium sulfate was removed by filtration, and the solvent was distilled off to obtain Compound (8) (orange, solid, 264.9 mg) at a crude yield of 97%. Compound (8) was not further purified, and was directly used for synthesis of Compound (25).

Synthesis of Compound (25)

Compound (2) (250.0 mg, 1.65 mmol) and acetic acid (8.0 ml) were added to the synthesized Compound (8), and the mixture was stirred at room temperature for 6 days. Then, an orange solid was precipitated. This solid was filtered by suction, and washed with water to obtain Compound (25) (orange, solid, 285 mg) at a yield of 57% (two-stage yield).

Synthesis of Compound (26)

Compound (25) (285.7 mg, 0.91 mmol) was weighed into a 100 ml eggplant flask, dried under reduced pressure, and then placed in an argon atmosphere. Dehydrated THF (9.1 ml) was added thereto, and the mixture was cooled to −78° C. Then, diisobutylaluminum hydride (1.0 M THF solution, 3.6 ml) was added dropwise thereto. The temperature was raised from −78° C. to 0° C., and the mixture was stirred at 0° C. for 3 hours. Thereafter, 1 N hydrochloric acid was added to adjust the pH to 3.0. The mixture was left to stand until normal temperature was reached and transferred to a separatory funnel. After extraction with THF, the organic layer was dried over sodium sulfate. Sodium sulfate was removed by filtration, and the solvent was distilled off to obtain Compound (26) (orange, solid, 180.6 mg) at a yield of 77%.

Synthesis of Compound (27)—

Compound (26) (180.6 mg, 0.70 mmol), triphenylphosphine (440.6 mg, 1.68 mmol), and phthalimide (247.1 mg, 1.68 mmol) were weighed into a 100 ml eggplant flask, dried under reduced pressure, and then placed in an argon atmosphere. Dehydrated THF (10.1 ml) was added, and the mixture was cooled to 0° C. Diisopropyl azodicarboxylate (0.880 ml, 1.68 mmol) was added dropwise thereto, and the temperature was raised from 0° C. to normal temperature. Then the mixture was stirred for 5 hours. After stirring, the solvent was distilled off, and The resultant residue was subjected to silica gel column chromatography (hexane: ethyl acetate=2:1) to obtain Compound (27) (orange, solid, 208.3 mg) at 57%.

Synthesis of Compound (2-5-6)

Compound (24) (208.3 mg, 0.40 mmol) was weighed into a 30 ml two-necked eggplant flask and dried under reduced pressure. Then, ethanol (2.1 ml) was added thereto under an argon atmosphere. Ethylenediamine (107.0 μl, 1.60 mmol) was added dropwise at room temperature. Then the temperature was raised, and the mixture was stirred for 3 days under reflux. After left to cool to room temperature, the mixture was transferred to a separatory funnel, water was added thereto, and the mixture was extracted with dichloromethane. Next, 1 N hydrochloric acid was added to the organic layer, and an extraction operation was performed with the separatory funnel. An aqueous sodium hydroxide solution was added to the obtained aqueous layer to make the aqueous layer basic (pH=11), then the aqueous layer was transferred to a separatory funnel, extracted with dichloromethane, and dried over sodium sulfate. Sodium sulfate was removed by filtration, and the solvent was distilled off. Then the obtained residue was subjected to silica gel column chromatography (methanol:aqueous ammonia=100:1), and Compound (2-5-6) (orange, solid, 41.9 mg) was obtained at 40%.

trans-Azobenzene Form (2-5-6)

$^1$H-NMR (400 MHz, CDCl$_3$)δ(ppm): 2.69 (s, 3H), 3.89 (s, 2H), 3.96 (s, 2H), 7.31-7.32 (m, 2H), 7.45 (d, 2H, J=8.28 Hz), 7.58 (s, 1H), 7.89 (d, 2H, J=8.32 Hz)

$^{13}$C-NMR (100 MHz, CDCl$_3$)δ(ppm): 17.1, 46.1, 46.2, 113.8, 123.1, 127.7, 129.6, 131.4, 136.5, 141.7, 146.2, 150.7, 152.0

TABLE 3

| | Absorption efficiency (%) | | Release efficiency (%) |
| Compound | Air bubbling | CO$_2$ bubbling | |
| --- | --- | --- | --- |
| Example 3 | Compound (1-2) | — | 90 | 39 |
| Example 4 | Compound (2-1-1) | — | 86 | 40 |
| Example 5 | Compound (2-3-1) | — | — | *30 |
| Example 6 | Compound (2-4-1) | — | 71 | 31 |
| Example 7 | Compound (2-5-6) | — | 63 | 12 |

Description of Table 3

As described above, only in Example 5, the method of evaluating the absorption capacity and release capacity of carbon dioxide is different from those in other Examples and Comparative Examples. Thus the value of the release efficiency obtained in Example 5 is marked with "*".

From Table 3, it was found that the compounds obtained in Examples had the absorption capacity and release capacity of carbon dioxide.

Next, Compound (1-1-1) obtained in Example 1 was used to evaluate CO$_2$ release efficiency in use of simulated sunlight. A specific evaluation method is as follows.

(Evaluation of CO$_2$ Release Efficiency Via Simulated Sunlight)

The same operations as in the calculation of the CO$_2$ release efficiency using NDIR (non-dispersive infrared absorption method) via UV irradiation were conducted, except that simulated sunlight was irradiated using a solar simulator (AM 1.5, 365 nm, lamp house: USHIO Optical ModuleX MS-35 AAA, compatible lamp: UXL-500 SX2) for the release of carbon dioxide.

As a result of the evaluation conducted by the method described above, the CO$_2$ release efficiency of Compound (1-1-1) obtained in Example 1 via simulated sunlight was 29%.

From the above, it is found that the compound obtained in Example 1 is a compound capable of absorbing and releasing carbon dioxide using simulated sunlight.

The disclosure of Japanese Patent Application No. 2019 036824 filed on Feb. 28, 2019 is incorporated herein by reference in its entirety.

All documents, patent applications, and technical standards described in the present description are incorporated herein by reference to the same extent as if each document, patent application, and technical standard were specifically and individually indicated to be incorporated by reference.

The invention claimed is:
1. A carbon dioxide collection method in which carbon dioxide is collected using a carbon dioxide absorption/release agent comprising a compound represented by Formula (1):

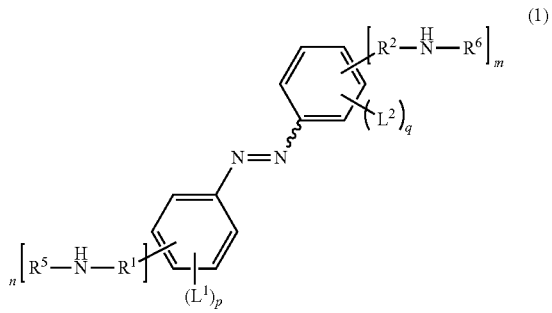

wherein, in Formula (1), each of L$^1$ and L$^2$ independently represents an alkyl group having from 1 to 20 carbon atoms, an alkoxy group having from 1 to 20 carbon atoms, NH$_2$, NHR$^3$, NR$^3$R$^4$, an ester group, a carboxy group, an amide group, a cyano group, a nitro group, a halogen atom, an acyl group, CF3, O(CH$_2$)$_t$OCH$_3$, a carbamate group, or an aryl group, provided that l represents 1 or 2, each of p and q independently represents an integer from 0 to 4, each of R$^1$ and R$^2$ independently represents a divalent hydrocarbon group having from 1 to 10 carbon atoms, at least one hydrogen atom of the divalent hydrocarbon group may be substituted with an alkyl group, an aryl group, an ester group, a carboxy group, an amide group, a cyano group, a nitro group, a halogen atom, an acyl group, CF$_3$, O(CH$_2$)$_t$OCH$_3$, a carbamate group, or an alkoxy group, each of $R^3$ and $R^4$ independently represents an alkyl group, an aryl group, an acyl group, an ester group, an alkylsulfonyl group, or an arylsulfonyl group, each of $R^5$ and $R^6$ independently represents a hydrogen atom, an alkyl group having from 1 to 20 carbon atoms, or an aryl group, and each of n and m independently represents an integer from 0 to 5, provided that n+m≥1.

2. The carbon dioxide collection method according to claim 1, comprising:

immersing the carbon dioxide absorption/release agent in a solvent, and bringing a fluid containing carbon dioxide into contact with the carbon dioxide absorption/release agent after the immersion.

3. The carbon dioxide collection method according to claim 2, wherein the solvent is at least one selected from the group consisting of chloroform, toluene, and acetonitrile.

4. The carbon dioxide collection method according to claim 2, further comprising irradiating the carbon dioxide absorption/release agent with ultraviolet light having a wavelength of from 300 nm to 400 nm, sunlight, or simulated sunlight to release absorbed carbon dioxide from the carbon dioxide absorption/release agent.

5. The carbon dioxide collection method according to claim 4, further comprising irradiating the carbon dioxide absorption/release agent with visible light having a wavelength of from 400 nm to 570 nm, or leaving the carbon dioxide absorption/release agent in a solution at room temperature for a certain period of time to bring the carbon dioxide absorption/release agent into a state in which it is capable of absorbing carbon dioxide.

* * * * *